United States Patent [19]
Clark

[11] Patent Number: 5,597,797
[45] Date of Patent: Jan. 28, 1997

[54] METHOD FOR TREATMENT OR PREVENTION OF OBESITY

[75] Inventor: Ross G. Clark, Pacifica, Calif.

[73] Assignee: Genentech, Inc., South San Francisco, Calif.

[21] Appl. No.: 150,090

[22] PCT Filed: Oct. 26, 1993

[86] PCT No.: PCT/US93/10259

§ 371 Date: Nov. 19, 1993

§ 102(e) Date: Nov. 19, 1993

[87] PCT Pub. No.: WO91/18621

PCT Pub. Date: Dec. 12, 1991

[51] Int. Cl.$^6$ .......................... A61K 38/00; A61K 37/24; C07K 14/00
[52] U.S. Cl. ................................. 514/12; 514/21
[58] Field of Search ........................... 514/12, 21

[56] References Cited

U.S. PATENT DOCUMENTS

| | | | |
|---|---|---|---|
| 4,792,546 | 12/1988 | Baker | 514/12 |
| 4,857,505 | 8/1989 | Arendt | 514/12 |
| 4,988,675 | 1/1991 | Froesch et al. | 514/12 |
| 5,126,324 | 6/1992 | Clark et al. | 514/12 |
| 5,183,660 | 2/1993 | Ikeda et al. | |
| 5,187,151 | 2/1993 | Clark et al. | 514/12 |

FOREIGN PATENT DOCUMENTS

| | | |
|---|---|---|
| 331630 | 6/1989 | European Pat. Off. |
| 0331630 | 9/1989 | European Pat. Off. |
| 473084 | 3/1992 | European Pat. Off. |
| 0473084 | 3/1992 | Japan . |
| WO91/18621 | 12/1991 | WIPO . |
| WO92/04489 | 3/1992 | WIPO . |
| WO92/11838 | 7/1992 | WIPO . |
| WO92/13556 | 8/1992 | WIPO . |
| 9213536 | 8/1992 | WIPO . |
| WO93/00109 | 1/1993 | WIPO . |

OTHER PUBLICATIONS

"Insulin–like growth factor 1 (IGF–1) for growth hormone (GH) insensitivity in Sweden" *Scrip* p. 24 (Jul. 8, 1994).
"Launch of Igef in Sweden" *Scrip* p. 23 (Jul. 12, 1994).
Furlanetto et al., "Estimation of somatomedin–C levels in normals and patients with pituitary disease by radioimmunoassay" *J. Clin. Invest.* 60:648–567 (1977).
Horner and Hintz, "Further comparisons of the [$^{125}$I] somatomedin A and the [$^{125}$I] somatomedin C radioreceptor assays of somatomedin peptide" *J. Clin. Endocrin. and Metab.* 48(6):959–963 (1979).
Hussain et al., "Comparison of the effects of growth hormone and insulin–like growth factor I on substrate oxidation and on insulin sensitivity in growth hormone–deficient humans" *J. Clin. Invest.* 94:1126–1133 (1994).
Jabri et al., "Adverse effects of recombinant human insulin–like growth factor I in obese insulin–resistant type II diabetic patients" *Diabetes* 43:369–374 (1994).

Kerr et al., "Effect of insulin–like growth factor–1 on the responses to and recognition of hypoglycemia in humans" *J. Clin. Invest.* 91:141–147 (1993).
Kolaczynski and Caro, "Insulin–like growth factor–1 therapy in diabetes: physiologic basis, clinical benefits, and risk" *Ann. Intern Med.* 120:47–55 (1994).
Kuzuya et al., "Trial of insulinlike growth factor 1 therapy for patients with extreme insulin resistance syndromes" *Diabetes* 42:696–705 (1993).
Lo et al., "Simultaneous treatment with IGF–I and GH additively increased anabolism in parenterally fed rats" *Am. J. Physiol.* 269:E368–E376 (1995).
Schalch et al., "Short–term effects of recombinant human insulin–like growth factor I on metabolic control of patients with type II diabetes mellitus" *J. Clin. Endocrin. and Metab.* 77(6):1563–1568 (1993).
Schoenle et al., "Recombinant human insulin–like growth factor I(rhIGF I) reduces hyperglycaemia in patients with extreme insulin resistance" *Diabetologia* 34:675–679 (1991).
Thompson et al., "The effects of recombinant human insulin–like growth factor–I and growth hormone on body composition in elderly women" *J. Clin. Endocrin. and Metab.* 80(6):1845–1852 (1995).
Usala et al., "Brief report: treatment of insulin–resistant diabetic ketoacidosis with insulin–like growth factor I in an adolescent with insulin–dependent diabetes" *New England J. of Medicine* 327(12):853–857 (1992).
Wilson et al., "Somatomedins in pregnancy: a cross–sectional study of insulin–like growth factors I and II and somatomedin peptide content in normal human pregnancies" *J. Clin. Endocrin. and Metab.* 55(5):858–861 (1982).
Zenobi et al., "Insulin–like growth factor–I improves glucose lipid metabolism in type 2 diabetes mellitus" *J. Clin. Invest.* 90:2234–2241 (1992).
Balasse, E., "Influence of Norepinephrine, Growth Hormone and Fasting on FFA Mobilization and Glucose Metabolism in Lean and Obese Subjects" *Diabetologia* 4:20–25 (1968).
Ballard et al., "Effects of IGF–1 and IGF Analogs on Growth During Catabolic States in Rats" *Modern Concepts of Insulin–Like Growth Factors,* Spencer, Ed., Elsevier Science Publ. Co. pp. 617–627 (1991).
Baxter, R. C., "The Somatomedins: Insulin–Like Growth Factors" *Advances in Clin Chem.* 25:49–115 (1986).
Bolinder et al., "Studies of Acute Effects of Insulin–Like Growth Factors I and II in Human Fat Cells" *J. Clin. Endocrinol. Metab.* 65(4):732–737 (1987).jf124c

*Primary Examiner*—Howard E. Schain
*Assistant Examiner*—P. Lynn Touzeau
*Attorney, Agent, or Firm*—Janet E. Hasak

[57] ABSTRACT

A method is disclosed for treating obese mammals or preventing obesity from occurring in mammals. This method involves administering to the mammal an effective amount of growth hormone in combination with an effective amount of IGF-I. Preferably, the growth hormone is given so as to have a maintained, continual therapeutically effective presence in the blood, such as by continuous infusion or frequent injections, or by use of a long-acting formulation.

20 Claims, 20 Drawing Sheets

OTHER PUBLICATIONS

Bray et al., "Effects of Triiodothyronine, Growth Hormone and Anabolic Steroids on Nitrogen Excretion and Oxygen Consumption of Obese Patients" *J. Clin. Endocrinol.* 33:293–300 (1971).

Bray, G. A., "Calorigenic Effect of Human Growth Hormone in Obesity" *J. Clin Endocrinol.* 29:119–122 (1969).

Bray, G. A., "Drug Treatment of Obesity" *Am. J. Clin. Nutr.* 55:538s–544s (1992).

Bray, G. A., "Treatment of Obesity: A Nutrient Balance/Nutrient Partition Approach" *Nutrition Reviews* 49(2):33–45 (1991).

Carlsson et al., "Growth Hormone and Growth in Diabetic Rats: Effects of Insulin and Insulin–Like Growth Factor–I Infusions" *J. Endocrinol.* 122:661–670 (1989).

Chalew et al., "Reduction of Plasma Insulin Levels does not Restore Concentration of Growth Hormone to Normal in Obese Children" *Intl. J. Obes.* 16:459–463 (1992).

Clark and Cronin, "The Effect of IGF–I on Body Growth and Chemical Composition in Hypophysectomized Rats" *Second International IGF Symposium, San Francisco, CA* (1991).

Clemmons and Underwood, "Somatomedin–C/Insulin–Like Growth Factor I in Acromegaly" *Clinics in Endocrinol. Metab.* 15(3):629–653 (1986).

Clemmons et al., "Growth Hormone Administration Conserves Lean Body Mass During Dietary Restriction in Obese Subjects" *J. Clin. Endocrinol.* 64(5):878–883 (1987).

Cocchi et al., "Sexual Dimorphism of Growth Hormone (GH) Responsiveness to GH–Releasing Hormone (GHRH) in Obese Rats" *Pharmacol. Res.* 25(2):336–337 (1992).

Collipp et al, "Body Composition Changes in Children Receiving Human Growth Hormone" *Metabolism* 22(4):589–595 (1973).

Conover et al., "Insulin Regulation of Insulin–Like Growth Factor Binding Protein–1 in Obese and Nonobese Humans" *J. Clin. Endocrinol.* 74(6):1355–1360 (1992).

Cordido et al., "Cholinergic Receptor Activation by Pyridostigmine Restores Growth Hormone (GH) Responsiveness to GH–Releasing Hormone Admin. in Obese Subjects: Evidence for Hypothalamic Somatostatinergic Participation . . . " *J. Clin. Endocrinol.* 68(2):290–293 (1989).

Cordido et al., "Study of Insulin–Like Growth Factor 1 in Human Obesity" *Horm. Res.* 36:187–191 (1991).

Cottam et al., "Body Growth, Carcass Composition, and Endocrine Changes in Lambs Chronically Treated with Recombinantly Derived Insulin–Like Growth Factor–I" *Endocrinology* 130(5):2924–2930 (1992).

Crist et al., "Body Composition Response to Exogenous GH During Training in Highly Conditioned Adults" *J. Appl. Physiol.* 65(2):579–584 (1988).

Crist et al., "Exogenous Growth Hormone Treatment Alters Body Composition and Increased Natural Killer Cell Activity in Women with Impaired Endogenous Growth Hormone Secretion" *Metabolism* 36(12):1115–1117 (1987).

Felig et al., "Metabolic Response to Human Growth Hormone During Prolonged Starvation" *J. Clin. Invest.* 50:411–421 (1971).

Froesch et al., "Therapeutic Potential of Insulin–Like Growth Factor 1" *TEM*, May/Jun. edition pp. 254–260 (1990).

Gama et al., "The Effect of Synthetic Very Low Calorie Diets on the GH–IGF–1 Axis in Obese Subjects" *Clinica Chimica Acta* 188:31–38 (1990).

Ghigo et al., "Arginine Potentiates But Does Not Restore the Blunted Growth Hormone Response to Growth Hormone–Releasing Hormone in Obesity" *Metabolism* 41:560–563 (1992).

Giaca et al., "Differential Effects of IGF–1 and Insulin on Glucoregulation and Fat Metabolism in Depancreatized Dogs" *Diabetes* 39:340–347 (1990).

Guler et al., "Recombinant human insulin–like growth factor 1 stimulates growth and has distinct effects on organ size in hypophysectomized rats" *Proc. Natl. Acad. Sci. USA* 85:4889–4893 (1988).

Guler et al., "Short–Term Metabolic Effects of Recombinant Human Insulin–Like Growth Factor I in Healthy Adults" *New England J. of Medicine* 317(3):137–140 (1987).

Guler et al., "Small Stature and Insulin–Like Growth Factors: Prolonged Treatment of Mini–Poodles with Recombinant Human Insulin–Like Growth Factor I" *Acta Endocrinologica* 121:456–464 (1989).

Hausman et al., "Effect of Somatropin Treatment of Adipore Cell Metabolism in Obese Zucker Rats with Restricted Caloric Intake" *FASEB J.* (Abstract 4248) 6(5):A1676 (Feb. 28, 1992).

Hochberg et al., "The Distal Axis of Growth Hormone (GH) in Nutritional Disorders: GH–Binding Protein, Insulin–Like Growth Factor–I (IGF–I), and IGF–I Receptors in Obesity and Anorexia Nervosa" *Metabolism* 41:106–112 (1992).Skottner et al., "Growth Responses in a Mutant Dwarf Rat to Human Growth Hormone and Recombinant Human Insulin–Like Growth Factor I" *Endocrinology* 124(5):2519–2526 (1989).

Slowinska–Srzednick et al., "An Abnormality of the Growth Hormone/Insulin–Like Growth Factor–I Axis in Women with Polycycstic Ovary Syndrome Due to Coexistent Obesity" *J. Clin. Endocrinol. and Metab.* 74(6):1432–1435 (1992).

Snyder et al., "Anabolic Effects of Growth Hormone in Obese Diet–Restricted Subjects are Dose Dependent" *Am. J. Clin. Nutr.* 52:431–437 (1990).

Snyder et al., "Dietary Carbohydrate Content Determines Responsiveness to Growth Hormone in Energy–Restricted Humans" *J. Clin. Endocrinol. Metab.* 69(4):745–752 (1989).

Snyder et al., "Treatment of Obese, Diet–Restricted with Growth Hormone for 11 Weeks: Effects on Anabolism, Lipolysis, and Body Composition" *J. Clin. Endocrinol. Metab.* 67(1):54–61 (1988).

Tanner et al., "Comparative Rapidity of Responses of Height, Limb Muscle and Limb Fat to Treatment with Human Growth Hormone in Patients with and without Growth Hormone Defiency" *Acta Endocrinologica* 84:681–696 (1977).

Tomas et al., "Increased Weight Gain, Nitrogen Retention and Muscle Protein Synthesis Following Treatment of Diabetic Rats with Insulin–Like Growth Factor (IGF–I) and des (1–3) IGF–I" *Biochemical Journal* 276:547–554 (1991).

Uthne et al., "Effects of Human Somatomedin Preparations on Membrane Transport and Protein Synthesis in the Isolated Rat Diaphragm" *J. Clin. Endocrinol. Metab.* 39(3):548–554 (1974).

Vance, M., "Growth Hormone for the Elderly?" *New England J. Med.* pp. 52–54 (1990).

Weintraub and Bray, "Drug Treatment of Obesity" *Med. Clin. of North America* 73(1):237–249 (1989).

Williams et al., "Impaired Growth Hormone Responses to Growth Hormone–Releasing Factor in Obesity" *New England J. of Med.* 311(22):1403–1407 (1984).

Williams et al., "Potential Therapeutic Indications for Growth Hormone–Releasing Hormone in Conditions other than Growth Retardation" *Pharmacotherapy* 6(6):311–318 (1986).

York and Bray, "Dependence of Hypothalamic Obesity on Insulin, the Pituitary and the Adrenal Gland" *Endocrinology* 90(4):885–894 (1972).

Zapf et al., "Acute Metabolic Effects and Half–Lives of Intravenously Administered Insulin–Like Growth Factors I and II in Normal Hypophysectomized Rats" *J. Clin. Invest.* 77:1768–1775 (1986).

Zapf et al., "Insulin–Like Growth Factors I and II: Some Biological Actions and Receptor Binding Characteristics of Two Purified Constituents of Nonsuppressible Insulin–Like Activity of Human Serum" *European Journal of Biochemistry* 87:285–296 (1978).

Zenobi et al., "Effects of insulin–like growth factor–I on glucose tolerance, insulin levels, and insulin secretion" *J. Clin. Invest.* 89:1908–1913 (1992).

Hussain et al., "Effects of Growth Hormone (GH) and Insulin–Like Growth Factor I (IGF–I) on Body Fuel Metabolism and Insulin Sensitivity in GH Deficient Humans" *Program and Abstract from Endocrine Society 75th Annual Meeting* (Abstract 1595) (Jun. 1993).

Jacob et al., "Simultaneous Insulin–Like Growth Factor I and Insulin Resistance in Obese Zucker Rats" *Diabetes* 41:691–697 (1992).

Jeevanandam et al., "Decreased Growth Hormone Levels in the Catabolic Phase of Severe Injury" *Surgery* 111:495–502 (1992).

Jorgensen, J., "Human Growth Hormone Replacement Therapy: Pharmacological and Clinical Aspects" *Endocrine Reviews* 12(3):189–207 (1991).

Jorgensen et al., "Beneficial Effects of Growth Hormone Treatment in GH–Deficient Adults" *Lancet* pp. 1221–1224 (Jun. 1989).

Jung and Chong, "The Management of Obesity" 35:11–20 (1991).

Jungman et al., "Somatomedin–C–Spiegel und Stimulation von Wachstumshormon und Nebennierenrindenfunktion durch Gabe von Releasing–Hormonen und Korperliche Belastung bei Patienten mit Adipositas" *Medizinische Klinik* 86(5):237–240 (1991).

Kopelman and Noonan, "Growth Hormone Response to Low Dose Intravenous Injections of Growth Hormone Releasing Factor in Obese and Normal Weight Women" *Clin. Endocrinol.* 24:157–164 (1986).

Kopelman et al., "Impaired Growth Hormone Response to Growth Hormone Releasing Factor and Insulin–Hypoglycaemia in Obesity" *Clin. Endocrinol.* 23:87–94 (1985).

Lee et al., "Successful Weight Loss with Protein–Sparing Modified Fast in a Morbidly Obese Boy with Panhypopituitarism, Diabetes Insipidus, and Defective Thirst Regulation" *Clin. Ped.* 31:234–236 (1992).

Loche et al., "Reduced Growth Hormone Response to Growth Hormone–Releasing Hormone in Children with Simple Obesity: Evidence for Somatomedin–C Mediated Inhibition" *Clin. Endocrinol.* 27:145–153 (1987).

Martin and Jeanreanaud, "Growth Hormone in Obesity and Diabetes: Inappropriate Hypothalamic Control of Secretion" *Intl. J. Obesity* 9(1):99–104 (1985).

Martin et al., "Growth Hormone Treatment Reduces Total Body Fat Accumulation in Zucker Obese Rats" *Intl. J. Obesity* 13:327–335 (1989).

Mautalen and Smith, "Lipolytic Effects of Human Growth Hormone in Resistant Obesity" *J. Clin. Endocrinol.* 25:495–498 (1965).

Novak et al., "Effect of HGH on Body Composition of Hypopituitary Dwarfs" *Mayo Clin. Proc.* 47:241–246 (1972).

Parra et al., "Body Composition in Hypopituitary Dwarfs Before and During Human Growth Hormone Therapy" *Metabolism* 28(8):851–857 (1979).

Pfadt and Angulo, "Changes in Body Composition and Energy Expenditure after Six Weeks' Growth Hormone Treatment" *Archives of Disease in Childhood* 66:1261–1263 (1991).

Raben and Hollenberg, "Effect of Growth Hormone on Plasma Fatty Acids" *J. Clin. Invest.* 38:484–488 (1959).

Reiter et al., "Decreased Growth Hormone Response to Growth Hormone–Releasing Hormone in Turner's Syndrome: Relation to Body Weight and Adiposity" *Acta Endocrinologica* 125:38–42 (1991).

Renier et al., "Dynamic of the GRF–Induced GH Response in Genetically Obese Zucker Rats: Influence of Central and Peripheral Factors" *Regulatory Peptides* 28:95–106 (1990).

Rissanen et al., "Risk of Disability and Mortality Due to Overweight in a Finnish Population" *Br. Med. J.* 301:835–837 (1990).

Ritschel, W. A., "In Vivo Animal Models for Bioavailability Assessment" *S.T.P. Pharma* 3(2): 125–141 (1987).

Rivlin, R., "The Dermatologist's Role in the Treatment of Obesity" *Intern. J. Dermatology* 15:446–449 (1976).

Rivlin, R., "Therapy of Obesity with Hormones" *New England J. of Medicine* 292(1):26–29 (1975).

Rivlin, R., "The Use of Hormones in the Treatment of Obesity" *Childhood Obesity*, Winick, Ed., John Wiley & Sons pp. 151–162 (1975).

Robinson and Clark, "The Secretory Pattern of GH and Its Significance for Growth in the Rat" *Growth Hormone–Basic and Clin. Aspects*, Isaksson et al., eds., Elsevier Science Publishers pp. 109–127 (1987).

Rolla et al., "Blockade of Cholinergic Muscarinic Receptors by Pirenzepine and GHRH–Induced GH Secretion in the Acute and Recovery Phase of Anorexia Nervosa and Atypical Eating Disorders" *Biol. Psychiatry* 29:1079–1091 (1991).

Rosskamp et al., "Circulating Somatomedin–C Levels and the Effect of Growth Hormone–Releasing Factor on Plasma Levels of Growth Hormone and Somatostatin–Like Immunoreactivity in Obese Children" *Eur. J. Pediatr.* 146:48–50 (1987).

Rudman et al., "Effects of Human Growth Hormone in Men over 60 Years Old" *New England J. Med.* 323(1):1–6 (1990).

Rudman, D., "Growth Hormone, Body Composition, and Aging" *J. Amer. Geriat. Soc* 3:800–807 (1985).

Salomon et al., "The Effects of Treatment with Recombinant Human Growth Hormone on Body Composition and Metabolism in Adults with Growth Hormone Deficiency" *New England J. of Medicine* 321(26):1797–1803 (1989).

Salter et al., "The Effects of Insulin and Somatotrophin on the Growth of Hypophysectomized Rats" *Can. J. Biochem. Physiol.* 35:913–922 (1957).

Siddiqui et al., "Developmental Patterns of Plasma Insulin–Like Growth Factor–I (IGF–I) and Body Growth in Mice from Lines Divergently Selected on the Basis of Plasma IGF–I" *J. Endocrinol.* 124:151–158 (1990).

Skaggs and Crist, "Exogenous Human Growth Hormone Reduces Body Fat in Obese Women" *Horm. Res.* 35:19–24 (1991).

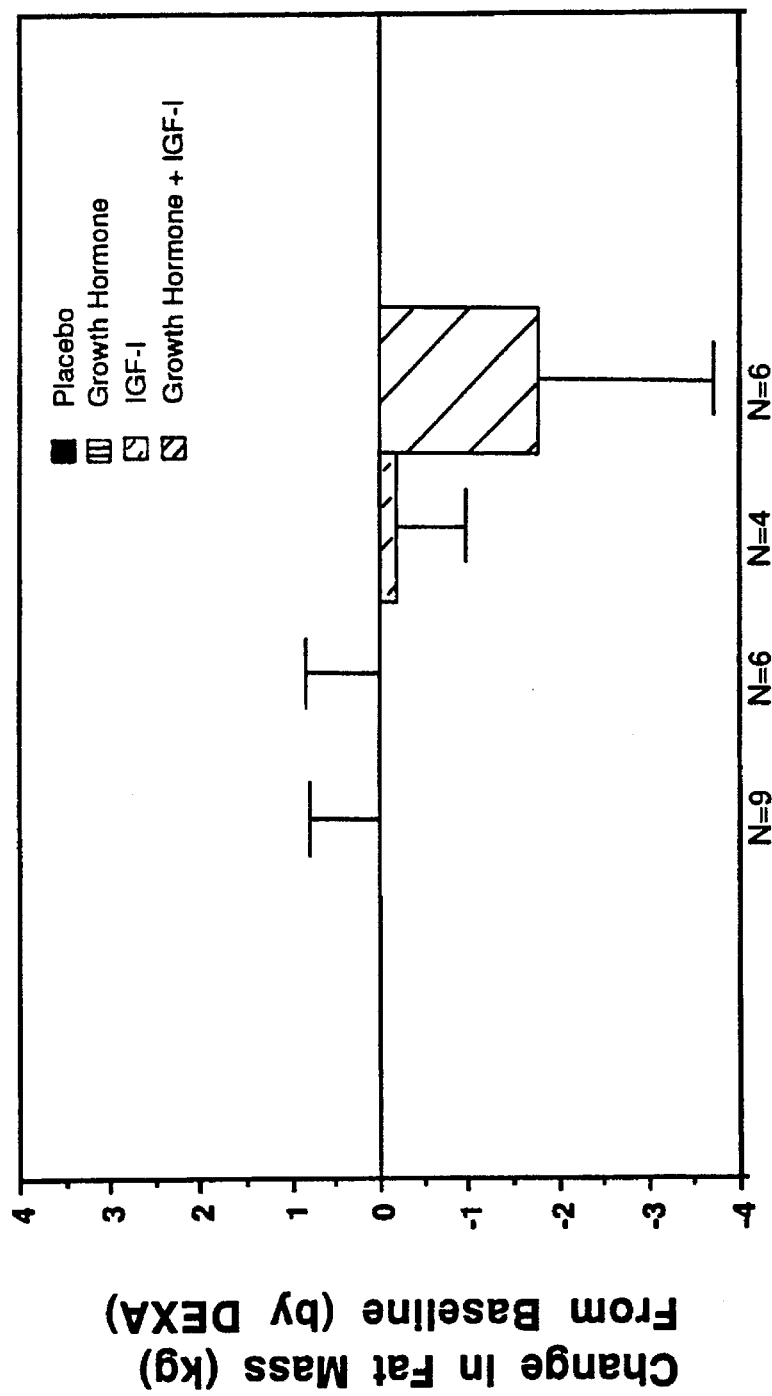

METHOD FOR TREATMENT OR PREVENTION OF OBESITY

BACKGROUND OF THE INVENTION

1. Field of the Invention

This invention relates to a method of restoring ideal population-based body composition in obese mammals or preventing obesity especially in humans.

2. Description of Background and Related Art

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, *Acanthosis nigricans*, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease. Rissanen et al., *British Medical Journal*, 301: 835–837 (1990).

Obese subjects tend to have low basal levels of growth hormone (GH) and fail to secrete significant amounts of GH in response to a variety of stimuli, including growth hormone releasing hormone (GHRH). Williams, *New Engl. J. Med.*, 311: 1403 (1984) Kopelman, *Clin. Endocrinol.*, 23: 87 (1985); Kopelman, *Clin. Endocrinol.*, 24: 157 (1986) Loche, *Clin. Endocrinol.*, 27: 145 (19871) Ghigo et al., *Metabolism*, 41: 560–563 (1992). The GH responsiveness to GHRH in obese rats shows sexual dimorphism. Cocchi et al., *Pharmacol. Res.*, 25: Suppl. 2, 336–337 (1992). This failure to secrete GH has been postulated to be the result of a hypothalamic disorder (Kopelman, 1986, supra), leading to a chronic state of somatostatin hypersecretion. Cordido, *J. Clin. Endocrinol. Metab.*, 68: 290 (1989). This defect in GH secretion appears to be a result rather than a cause of obesity, since it is, at least in part, reversible with weight reduction.

While it has been suggested that the refractoriness of obese subjects to release GH is due to the feedback inhibition operated by the elevated plasma levels of insulin-like growth factor (IGF-I) (Loche et al., *Clin. Endocrinol.*, 27: 145–153 [1987]), in fact, no correlation was found between IGF-I and indices of overweight. Cordido et al., *Horm. Res.*, 36: 187–191 (1991). Thus, adiposity is not associated with a decline in IGF-I levels. Hochberg et al., *Metabolism*, 41: 106–112 (1992); Gama et al., *Clin. Chim. Acta*, 188: 31–38 (1990); Rosskamp et al., *Eur. J. Pediatr.*, 146: 48–50 (1987). Further, impaired hGH stimulation in obese human subjects is not explained by an altered relationship between hGH and IGF-I levels. Jungmann et al., *Med. Klin.*, 86: 237–240 (1991). Nor does reduction in circulating insulin levels lead to a higher ability to secrete GH. Chalew et al., *Inter. J. Obesity*, 16:459–463 (1992).

Certain diseases such as diabetes mellitus, especially adult onset or Type II diabetes, show a much higher prevalence of obesity. It has been found that low IGFBP-1 levels in obesity are related to elevated insulin levels, which are, in turn, related to body fat distribution and insulin resistance. The chronically depressed levels of IGFBP-1 may promote IGF bioactivity as well as its feedback regulation of GH secretion, thus contributing to the metabolic and mitogenic consequences of obesity. Conover et al., *J. Clin. Endocrinol. Metab.*, 74: 1355–1360 (1992).

Existing therapies for obesity include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery. Jung and Chong, *Clinical Endocrinology*, 35: 11–20 (1991); Bray, *Am. J. Clin. Nutr.*, 55: 538S–544S (1992). Protein-sparing modified fasting has been reported to be effective in weight reduction in adolescents. Lee et al., *Clin. Pediatr.*, 31: 234–236 (April 1992). Caloric restriction as a treatment for obesity causes catabolism of body protein stores and produces negative nitrogen balance. Protein-supplemented diets, therefore, have gained popularity as a means of lessening nitrogen loss during caloric restriction. Because such diets produce only modest nitrogen sparing, a more effective way to preserve lean body mass and protein stores is needed. In addition, treatment of obesity would be improved if such a regimen also resulted in accelerated loss of body fat. Various approaches to such treatment include those discussed by Weintraub and Bray, *Med. Clinics N. Amer.*, 73: 237 (1989); Bray, *Nutrition Reviews*, 49: 33 (1991).

GH plays an important role in the regulation of somatic growth and metabolism. The metabolic effects of GH have been divided into early insulin-like effects, associated with enhanced glucose utilization and increased amino acid transport, and into anti-insulin-like effects, associated with the stimulation of lipolysis and depression of glucose utilization. GH promotes nitrogen conservation. Bray et al., *J. Clin. Endocrinol. Metab.*, 33: 293 (1971).

IGF-I production is under the dominant stimulatory influence of GH, and some of the IGF-I binding proteins are also influenced by GH. See Tanner et al., *Acta Endocrinol.*, 84: 681–696 (1977); Uthne et al., *J. Clin. Endocrinol. Metab.*, 39: 548–554 (1974). For general reviews of IGF-I, see Baxter, *Advances in Clinical Chemistry*, 25: 49 (1986); Clemmons and Underwood, *Clinics in Endocrin. and Metab.*, 15: 629 (1986). The use of IGF-I and GH by injection to produce weight gain and to have anabolic and growth-promoting effects in mammals, including diabetic patients, is disclosed by U.S. Pat. No. 5,126,324 issued Jun. 30, 1992.

GH is known to accelerate lipolysis in animals as well as in normal and obese humans. Raben and Hollenberg, *J. Clin. Invest.*, 38: 484 (1959); Mautalen and Smith, *J. Clin. Endocrinol. Metab.*, 25: 495 (1965); Felig et al., *J. Clin. Invest.*, 50: 411 (1971); Jorgenson, *Endocr. Reviews*, 12, (1991); Martin et al., *Inter, J. Obesity*, 13: 327–335 (1989); Pfadt and Angulo, *Arch. Dis. Child.*, 66: 1261 (1991); Jeevanandam et al., *Surgery*, 111: 495–502 (1992). GH was administered with a phenylethane derivative to increase weight gains and anti-lipogenic activity in animals. U.S. Pat. No. 4,792,546 issued Dec. 20, 1988. A lipolytic composition utilizing a growth factor such as nerve growth factor, epidermal growth factor, and fibroblast growth factor is described in WO 92/11838 published 23 Jul. 1992. The possibility of using GH to treat obesity is also discussed by Rivlin, "The Use of Hormones in the Treatment of Obesity," in *Childhood Obesity*, ed. Winick (John Wiley & Sons: New York, 1975), pp. 151–162, and Rivlin, *Intern. J. Dermatol.*, 15: 446–449 (1976).

Examples of models showing that administration of GH to obese individuals could stimulate lipolysis include hypophysectomized, ventromedial-hypothalamic-lesionedrats, where GH prevented both hyperphagia and development of obesity (York and Bray, *Endocrinology*, 90: 885–894 [1972]), and genetically obese Zucker fa/fa rats, which had reduced lipid deposition. Martin and Jeanrenaud, *Int. J. Obesity*, 9: 99–104 (1985). See also Williams and Frohman, *Pharma-*

*cotherapy*, 6: 311–318 (1986) and Rivlin, *New. Engl. J. Med.*, 292: 26 (1975).

Several studies of GH administration to GH-deficient children, many of whom are obese, demonstrated that one of the earliest and most noticeable changes was loss of adipose tissue. Novak et al., *Mayo Clin. Proc.*, 47: 241–246 (1972); Collipp et al., *Metabolism*, 22: 589–595 (1973); Parra et al., *Metabolism*, 28: 851–857 (1979). In addition, obese adults have elevated free fatty acids, indicating increased lipolysis, in response to an injection of GH. Mautalen and Smith, *J. Clin. Endocrinol.*, 25: 495–498 (1965); Blasse, *Diabetologia*, 4: 20–25 (1968); Bray, *Metab.*, 29: 119–122 (1969).

Further, GH injection to obese patients on a high carbohydrate diet produced more body fat loss than injection of vehicle. Snyder et al., *J. Clin. Endocrin. Metab.*, 69: 745 (1989). It had also been found that exogenous GH reduced body fat and increased fat-free mass in older women that have an impairment in endogenous GH release (Crist et al., *Metabolism*, 36: 1115–1117 [1987]), and in normosecretory physically fit adults. Crist et al., *J. Appl. Physiol.*, 65: 579–584 (1988). These changes occurred without dietary modification or alterations in physical activity patterns. GH was reported by at least one group to increase the oxidation of fat during caloric restriction. Bray, *J. Clin. Endocrinol. Metab.*, 29: 119 (1969). However, others (Clemmons et al., *J. Clin. Endocrinol. Metab.*, 64: 878–883 [1987]; Snyder et al., *J. Clin. Endocrinol. Metab.*, 67: 54–61 [1988]; Snyder et al., *Am. J. Clin. Nutr.*, 52: 431–437 [1990]) have not found a GH-induced enhancement of body fat loss when the hormone was administered to obese adults during a program of caloric restriction. It was found that exogenous GH reduces body fat in obese women in the apparent absence of significant kilocaloric restriction, which effect is unrelated to endogenous GH secretion or body composition. Skaggs and Crist, *Horm. Res.*, 35: 19–24 (1991).

Some of the manifestations of aging, including expansion of adipose-tissue mass, have been shown to be reduced by GH treatment three times a week. Rudman et al., *N. Eng. J. Med.*, 323: 1–6 (1990); Crist et al., *Metabolism*, 36: 1115–1117 (1987).

IGF-I is reported to lower blood glucose levels in rats and humans for use in treating diabetes and the secondary effects of hyperinsulinemia, including obese subjects. Froesch et al., *TEM*, May/June 1990, p. 254–260; Guler et al., *N. Engl. J. Med.*, 317: 137–140 (1987); U.S. Pat. No. 4,988,675 issued Jan. 29, 1991; Carisson et al., *J. Endocrin.*, 122: 661–670 (1989); Zenobi et al., *J. Clin. Invest.*, 89: 1908–1913 (1992). In contrast to GH, IGF-I and insulin have a known anti-lipolytic effect. Zapf et al., *J. Clin. Invest.*, 77: 1768–1755 (1986); Guler et al., *N. Engl. J. Med.*, 317: 137–140 (1987); Zapf et al, *Eur. J. Biochem.*, 87: 285–296 (1978); Bolinder et al., *Clin. Endocrinol. Metab.*, 65: 732–737 (1987); Giacca et al., *Diabetes*, 39: 340–347 (1990). Further, it has been observed that obese Zucker rats are resistant to the effects of IGF-I and insulin on glucose and amine acid metabolism. Jacob et al., *Diabetes*, 41: 691–697 (1992).

The most recent study of the effect of IGF-I on body composition was by Certain et al. (*Endocrinology*, 130: 2924–2930 [1992]), who injected recombinant human IGF-I (three times a day at 150 µg/kg/day for 8 weeks) in castrate male sheep fed a pelleted and lucerne chaff diet. Treatment caused plasma IGF-I levels to rise, plasma insulin to fall, and tibia, spleen, and kidney weights to increase. However, despite IGF-I having obvious efficacy, it had no detectable effect on body fat. These authors state that their results are consistent with their earlier studies (Siddiqui et al., *J. Endocrinol.*, 124: 151–158 [19901]) showing similar body composition at equal body weights in mice selected for high and low plasma IGF-I concentrations. They conclude that the effects of GH on reducing body fat are not mediated solely through circulating IGF-I.

In another study, a catabolic state was induced in young rats by diabetes, dexamethasone, or intestinal resection, and then the catabolic animals were treated with IGF-I or IGF-I analogues. Ballard et al., in *Modern Concepts of Insulin-Like Growth Factors*, ed. Spencer, p. 617–627 (1991). The authors reported that the IGFs caused a trend toward a lower percentage of body fat.

In a long-term study (Guler et al., *Acta Endo.*, 121: 456–464 [1990]), mini-poodles were treated for 130 days with 6 mg/day of recombinant human IGF-I. There was no change in overall body growth but there was a reduced body mass index, which the authors suggest might have been caused by IGF-I. However, they state that this suggestion is to be interpreted with great caution, and that recombinant human IGF-I may well alter carbohydrate and lipid metabolism in the opposite direction of GH.

In the hypophysectomized rat, IGF-I treatment, at doses that caused a large increase in body and organ weights, had no effect on the chemical composition of the skin or carcass. In particular, the percentage of fat was not changed by IGF-I treatment. Clark and Cronin, Abstract D8, *2nd International IGF Symposium*, San Francisco, Calif., 1991.

In a recent review summarizing the accumulated knowledge at that time of insulin and IGF-I activity on different tissues (Froesch et al., *TEM*, 254–260 [May/June 1990]), it is stated on page 256 that small doses of IGF-I may be expected not to affect adipose tissues and this was observed in the rat. They also state that IGF-I administration to the rat in vivo had much more marked effects on muscle than on adipose tissue, citing Zapf et al., *J. Clin. Invest.*, 77: 1768 [1986]. In humans, they state that, compared to insulin, the hypoglycemic potential of IGF-I is relatively greater than its anti-lipolytic potential, citing Guler et al., *N. Engl. J. Med.*, 317: 137 [1987].

It was also found that while insulin-treated hypophysectomized rats increased their food consumption more than untreated hypophysectomized rats (Salter et al., *Can. J. Biochem. Physiol.*, 35: 913 [1957]), food intake in young non-obese dwarf rats was unaffected by either GH or IGF-I infusions. Skottner et al., *Endocrinology*, 124: 2519–2526 (1989).

Data have demonstrated that many of the effects of GH in rodents are dependent on the pattern in which GH is administered. Robinson and Clark, in *Growth Hormone—Basic and Clinical Aspects*, eds. Isaksson et al., p, 109–127 (1987). Animals have been treated with GH in many different dose regimes. Continuous infusion of GH has been shown to reduce body fat in the genetically obese Zucker rat. Martin et al., April 1992, FASEB Meeting, Anaheim, Calif. In man, GH regimes of twice daily and daily, and once, twice, and three times a week, and "intermittent" regimes have been tested for their effects on body growth in GH-deficient children. The data demonstrate that frequent injections of GH (daily) are the regime of choice (this is now the accepted regime used in the clinic). The data in the rat also show that frequent injections of GH produce greater bone growth and weight gain than infrequent injections of GH, and that continuous exposure to GH by infusion is not as effective as frequent intermittent injections of GH. However, it has been disclosed that infusions of GH, alone or in combination with IGF-I, in amounts that maintain a continuous effective plasma GH concentration, are necessary to stimulate the immune system (GH-responsive lymphoid tissues) of a host mammal or avian. WO 93/00109 published 7 Jan. 1993.

Considering the high prevalence of obesity in our society and the serious consequences associated therewith as discussed above, any therapeutic drug potentially useful in reducing weight of obese persons could have a profound beneficial effect on their health. There is a need in the art for a drug that will reduce total body weight of obese subjects toward their ideal body weight without significant adverse side effects and that will help the obese subject maintain the reduced weight level.

It is therefore an object of the present invention to provide a treatment regimen that is useful in returning the body weight of obese subjects toward a normal, ideal body weight.

It is another object to provide a therapy for obesity that results in maintenance of the lowered body weight for an extended period of time.

It is yet another object to prevent obesity and, once treatment has begun, to arrest progression or prevent the onset of diseases that are the consequence of, or secondary to, the obesity, such as arteriosclerosis and polycystic ovarian disease.

These and other objects will be apparent to those of ordinary skill in the art.

SUMMARY OF THE INVENTION

Accordingly, the present invention provides a method for treating obesity or preventing obesity in a mammal comprising administering to the mammal an effective amount of IGF-I and GH. The GH is optimally administered such that its therapeutically effective concentration is maintained continuously in the blood of the mammal for the duration of the period of its administration. Such GH administration properly includes use of GH made long-acting either by prolonging the presence of GH in the blood or by causing a slow-release of GH from an injection site. GH administration that is continuous also includes administration by continuous infusion or by injections more frequent that once per day.

In one preferred mode of administration, the GH is covalently bonded via up to ten of the amino acid residues, preferably the N-terminal methionine or the lysine residues, of human GH (hGH), with higher substitutions generally increasing the circulatory life of the protein. Preferably such moieties are connected to the GH via an amide linkage formed from the 4-hydroxy-3-nitrobenzene sulfonate ester or the N-hydroxysuccinimide (NHS) ester of a polyethylene glycol (PEG), a monomethyl-substituted homopolymer of PEG, or a polyoxyethylene glycerol carboxylic acid. The most preferred polymer herein is PEG attached to up to 10 residues, preferably 2 to 8 PEG molecules per hGH molecule.

BRIEF DESCRIPTION OF THE DRAWINGS

FIG. 20 shows the effect of IGF-I, GH and a combination of GH and IGF-I on fat mass when administered subcutaneously to AIDS patients. The solid black bars indicate placebo, the bars with a black background having white slashes indicate GH, the speckled bars indicate IGF-I, and the bars with a white background having black slashes indicate GH and IGF-I. The number of patients treated per group are indicated by the N numbers below the bar graphs, and the y axis indicates the change in fat mass (kg) from baseline.

DESCRIPTION OF THE PREFERRED EMBODIMENTS

A. Definitions

Figure 1:
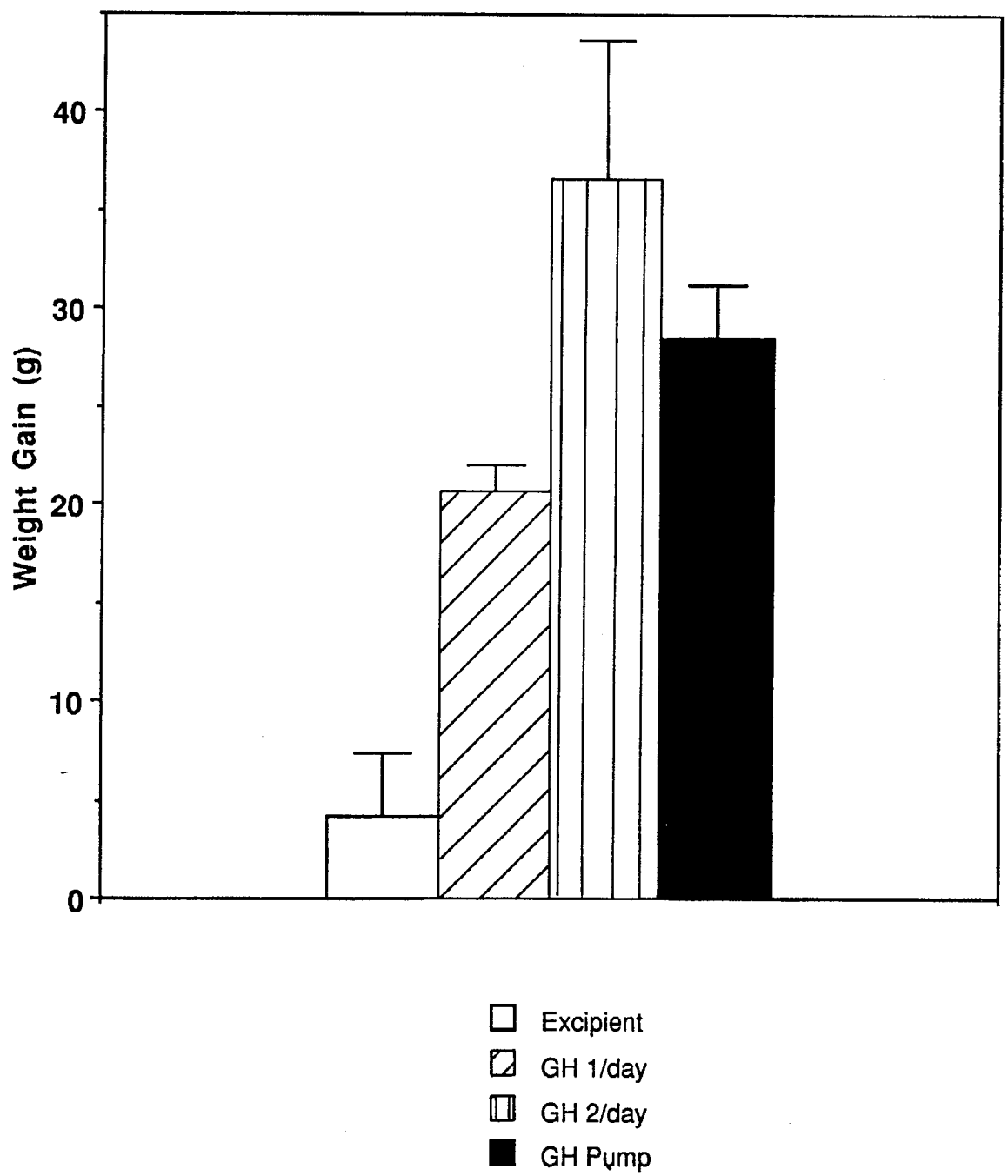
FIG. 1 shows the body weight gain in young (6–9-week old) non-obese dw/dw female rats over eight days when given excipient (open bars), GH injections once per day (wide diagonal lines), GH injections twice per day (narrow diagonal lines), and GH by mini-pump infusion (solid bars). All Figures and text show means±standard deviations, with statistical significances being described in the text.

As used herein, "obesity" refers to a condition whereby a mammal has a Body Mass Index (BMI), which is calculated as weight (kg) per height$^2$ (meters), of at least 25.9. Conventionally, those persons with normal weight have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

"Treatment" refers to reducing the BMI of the mammal to less than about 25.9, and maintaining that weight for at least 6 months. The treatment suitably results in a reduction in food or caloric intake by the mammal.

"Prevention" refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

Thus, in one aspect, this invention relates to the inhibition and/or complete suppression of lipogenesis in obese mammals, i.e., the excessive accumulation of lipids in fat cells, which is one of the major features of human and animal obesity, as well as loss of total body weight. In another aspect, the invention ameliorates the conditions that are a consequence of the disease, such as preventing or arresting the progression of polycystic ovarian disease so that the patient is no longer infertile, and increasing the insulin sensitivity and/or decreasing or eliminating the need or usage of insulin in a diabetic patient, e.g., one with adult-onset diabetes or Type II diabetes.

"Mammals" include animals of economic importance such as bovine, ovine, and porcine animals, especially those that produce meat, as well as domestic animals, sports animals, zoo animals, and humans, the latter being preferred. The term "non-adult" refers to mammals that are from perinatal age up until the age of puberty, the latter being those that have not yet reached full growth potential. Obese humans that are "GH deficient" are those that lack GH function, such as those that are pituitary deficient, as well as those that have GH receptor or GH binding protein deficiencies.

As used herein, "GH" refers to growth hormone from any species, including bovine, ovine, porcine, equine, and preferably human, in native-sequence or in variant form, and from any source, whether natural, synthetic, or recombinant. Preferred herein for animal use is that form of GH from the particular species being treated, such as porcine GH to treat pigs, ovine GH to treat sheep, bovine GH to treat cattle, etc.

Preferred herein for human use is human native-sequence, mature GH with or without a methionine at its N-terminus. Also preferred is recombinant hGH, i.e., that produced by means of recombinant DNA technology. More preferred is methionyl human growth hormone (met-hGH) produced in *E. coli*, e.g., by the process described in U.S. Pat. No. 4,755,465 issued Jul. 5, 1988 and Goeddel et al., *Nature*, 282: 544 (1979). Met-hGH, which is sold under the trademark PROTROPIN® by Genentech, Inc., is identical to the natural polypeptide, with the exception of the presence of an N-terminal methionine residue. This added amino acid is a result of the bacterial protein synthesis process. Also preferred is a recombinant hGH available to clinical and research investigators from Genentech, Inc. under the trademark NUTROPIN®, and commercially available from Eli Lilly. This latter hGH lacks this methionine residue and has an amino acid sequence identical to that of the natural hormone. See Gray et al., *Biotechnology*, 2: 161 (1984). Both methionyl hGH and hGH have equivalent potencies and pharmacokinetic values. Moore et al., *Endocrinology*, 122: 2920–2926 (1988). Another appropriate hGH candidate is an hGH variant that is a placental form of GH with pure somatogenic and no lactogenic activity as described in U.S. Pat. No. 4,670,393 issued 2 Jun. 1987. Also included are GH variants as described in WO 90/04788 published 3 May 1990 and WO 92/09690 published 11 Jun. 1992.

As used herein, "IGF-I" refers to insulin-like growth factor from any species, including bovine, ovine, porcine, equine, arian, and preferably human, in native-sequence or in variant form, and from any source, whether natural, synthetic, or recombinant. IGF-I has been isolated from human serum and produced recombinantly. See, e.g., EP 123,228 and 128,733.

Preferred herein for animal use is that form of IGF-I from the particular species being treated, such as porcine IGF-I to treat pigs, ovine IGF-I to treat sheep, bovine IGF-I to treat cattle, etc. Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations. Also preferred for use is IGF-I that has a specific activity greater than about 14,000 units/mg as determined by radioreceptor assay using placenta membranes, such as that available from KabiGen AB, Stockholm, Sweden.

The preferred IGF-I variants are those described in U.S. Pat. No. 5,077,276 issued Dec. 31, 1991, in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1-3)-IGF-I, or des-IGF-I).

The preference that the GH administration be such that "its therapeutically effective concentration is maintained continuously in the blood of the mammal for the duration of the period of its administration" refers to GH administration, whether by a route, formulation, regimen, mode, schedule, or other means, that results in a therapeutical)y effective plasma or serum concentration of GH during the time when the GH is administered to the mammal. Under this definition, the GH is present at a concentration sufficient and effective to treat obesity as defined herein.

B. Modes for Carrying Out the Invention

The GH in combination with IGF-I is directly administered to the mammal by any suitable technique, including parenterally, intranasally, orally, or by absorption through the skin. They need not be administered by the same route and can be administered locally or systemically. The specific route of administration of each agent will depend, e.g., on the medical history of the patient, including any perceived or anticipated side or reduced anabolic effects using hGH or IGF-I alone. Examples of parenteral administration include subcutaneous, intramuscular, intravenous, intraarterial, and intraperitoneal administration.

The GH and IGF-I are administered so as to be in effective amounts. The GH may be administered non-continuously, such as at particular times (e.g., once daily) in the form of an injection of a particular dose, where there will be a rise in plasma GH concentration at the time of the injection, and then a drop in plasma GH concentration until the time of the next injection. Another non-continuous administration method results from the use of many implant devices available that provide a discontinuous release of active ingredient, such as an initial burst, and then a lag before release of the active ingredient. See, e.g., U.S. Pat. No. 4,767,628, col. 2, lines 19–37.

However, more preferably the GH is administered so as to have a continual presence in the blood that is maintained for the duration of the administration of the GH. This is most preferably accomplished by means of continuous infusion via, e.g., mini-pump such as osmotic mini-pump. Alternatively, it is properly accomplished by use of frequent injections of GH (i.e., more than once daily, for example, twice or three times daily).

In yet another embodiment, GH may be administered using long-acting GH formulations that either delay the clearance of GH from the blood or cause a slow-release of GH from, e.g., an injection site. The long-acting formulation that prolongs GH plasma clearance may be in the form of GH complexed, or covalently conjugated (by reversible or irreversible bonding), to a macromolecule such as one or more of its binding proteins (WO 92/08985 published 29 May 1992) or a water-soluble polymer selected from PEG and polypropylene glycol (POG) homopolymers and polyoxyethylene polyols, i.e., those that are soluble in water at room temperature.

One well characterized GH binding protein is the high-affinity growth hormone binding protein (GHBP) constituting the extracellular domain of the GH receptor that circulates in blood and functions as a GHBP in several species (Ymer and Herington, *Mol. Cell. Endocrino.*, 41: 153 [1985]; Smith and Talamantes, *Endocrinology*, 123: 1489–1494 [1988]; Emtner and Roos, *Acta Endocrinologica (Copenh.)*, 122: 296–302 [1990]), including man. Baumann et al., *J. Clin. Endocrinol. Metab.*, 62: 134–141 (1986); EP 366,710 published 9 May 1990; Herington et al., *J. Clin. Invest.*, 77: 1817–1823 (1986); Leung et al., *Nature*, 330: 537–543 (1987). A second BP with lower affinity for GH has also been described that appears to be structurally unrelated to the GH receptor. Baumann and Shaw, *J. Clin. Endocrinol. Metab.*, 70: 680–686 (1990).

Alternatively, the GH may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides, The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1–C4 alkyl group, and most preferably a methyl group. Most preferably, the polymer is an unsubstituted homopolymer of PEG, a monomethyl-substituted homopolymer of PEG (mPEG), or polyoxyethylene glycerol (POG), and has a molecular weight of about 5000 to 40,000.

The GH is covalently bonded via one or more of the amino acid residues of the GH to a terminal reactive group on the polymer, depending mainly on the reaction conditions, the molecular weight of the polymer, etc. The polymer with the reactive group(s) is designated herein as activated polymer. The reactive group selectively reacts with free amino or other reactive groups on the GH. It will be understood, however, that the type and amount of the reactive group chosen, as well as the type of polymer employed, to obtain optimum results, will depend on the particular GH employed to avoid having the reactive group react with too many particularly active groups on the GH. As this may not be possible to avoid completely, it is recommended that generally from about 0.1 to 1000 moles, preferably 2 to 200 moles, of activated polymer per mole of protein, depending on protein concentration, is employed. The final amount of activated polymer per mole of protein is a balance to maintain optimum activity, while at the same time optimizing, if possible, the circulatory half-life of the protein.

While the residues may be any reactive amino acids on the protein, such as one or two cysteines or the N-terminal amino acid group, preferably the reactive amino acid is lysine, which is linked to the reactive group of the activated polymer through its free epsilon-amino group, or glutamic or aspartic acid, which is linked to the polymer through an amide bond.

The covalent modification reaction may take place by any appropriate method generally used for reacting biologically active materials with inert polymers, preferably at about pH 5–9, more preferably 7–9 if the reactive groups on the GH are lysine groups. Generally, the process involves preparing an activated polymer (with at least one terminal hydroxyl group), preparing an active substrate from this polymer, and thereafter reacting the GH with the active substrate to produce the GH suitable for formulation. The above modification reaction can be performed by several methods, which may involve one or more steps. Examples of modifying agents that can be used to produce the activated polymer in a one-step reaction include cyanuric acid chloride (2,4,6-trichloro-S-triazine) and cyanuric acid fluoride.

In one embodiment the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group that is capable of reacting with the GH. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted at elevated temperatures, preferably about 100°–110° C. for four hours, with glutaric anhydride. The monomethyl PEG-glutaric acid thus produced is then reacted with N-hydroxysuccinimide in the presence of a carbodiimide reagent such as dicyclohexyl or isopropyl carbodiimide to produce the activated polymer, methoxypolyethylene glycolyl-N-succinimidyl glutarate, which can then be reacted with the GH. This method is described in detail in Abuchowski et al., *Cancer Biochem. Biophys.*, 7: 175–186 (1984). In another example, the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described by Bhatnagar et al., *Peptides: Synthesis-Structure-Function, Proceedings of the Seventh American Peptide Symposium,* Rich et al. (eds.) (Pierce Chemical Co., Rockford Ill., 1981), p. 97–100, and in Nitecki et al., *High-Technology Route to Virus Vaccines* (American Society for Microbiology: 1986) entitled "Novel Agent for Coupling Synthetic Peptides to Carriers and Its Applications."

Specific methods of producing hGH conjugated to PEG include the methods described in U.S. Pat. No. 4,179,337 on PEG-hGH and U.S. Pat. No. 4,935,465, which discloses PEG reversibly but covalently linked to hGH. Other specific methods for producing PEG-hGH include the following:

PEGylation with methoxypolyethylene glycol aldehyde (Me-PEG aldehyde) by reductive alkylation and purification is accomplished by adding to 2 mg/ml of hGH in PBS pH 7.0, 5 mM of Me-PEG aldehyde-5000 (molecular weight 5000 daltons) and 20 mM of NaCNBH3 and gently mixing at room temperature for 3 hours. Ethanolamine is then added to 50 mM to reductively amidate the remaining unreacted Me-PEG. The mixture is separated on an anion-exchange column, FPLC Mono Q. The surplus unreacted Me-PEG does not bind to the column and can then be separated from the mixture. Two main PEGylated hGH fractions are obtained with apparent molecular weights of 30K and 40K on reduced SDS-PAGE, vs. 20K of the unreacted hGH. hGH-hGH binding protein complex is PEGylated in the same manner to give a derivative of 150K by gel filtration.

PEGylation with N-hydroxysuccinimidyl PEG (NHS-PEG) and purification are accomplished by adding NHS-PEG at a 5-fold molar excess of the total lysine concentration of hGH to a solution containing 2 mg/ml of hGH in 50 mM of sodium borate buffer at pH 8.5 or PBS at pH 7, and mixing at room temperature for one hour. Products are separated on a Superose 12 sizing column and/or Mono Q of FPLC. The PEGylated hGH varies in size depending on the pH of the reaction from approximately 300 Kd for the reaction run at pH 8.5 to 40 Kd for pH 7.0 as measured by gel filtration. The hGH-hGH binding protein complex is also PEGylated the same way with a resulting molecular weight of 400 to 600 Kd from gel filtration.

PEGylation of the cysteine mutants of hGH with PEG-maleimide is accomplished by preparing a single cysteine mutant of hGH by site-directed mutagenesis, secreting it from an *E. coli* 16C9 strain (W3110 delta tonA phoA delta E15 delta (argF-lac)169 deoC2 that does not produce the deoC protein and is described in U.S. Ser. No. 07/224,520 filed 26 Jul. 1988, now abandoned, the disclosure of which is incorporated herein by reference) and purifying it on an anion-exchange column. PEG-maleimide is made by reacting monomethoxyPEG amine with sulfo-MBs in 0.1M sodium phosphate pH 7.5 for one hour at room temperature and buffer exchanged to phosphate buffer pH 6.2. Next hGH with a free extra cysteine is mixed in for one hour and the final mixture is separated on a Mono Q column as in Me-PEG aldehyde PEGylated hGH.

As ester bonds are chemically and physiologically labile, it may be preferable to use a PEG reagent in the conjugating reaction that does not contain ester functionality. For example, a carbamate linkage can be made by reacting PEG-monomethyl ether with phosgene to give the PEG-chloroformate. This reagent could then be used in the same manner as the NHS ester to functionalize lysine side-chain amines. In another example, a urea linkage is made by reacting an amino-PEG-monomethyl ether with phosgene. This would produce a PEG-isocyanate that will react with lysine amines.

A preferred manner of making PEG-hGH, which does not contain a cleavable ester in the PEG reagent, is described as follows: Methoxypoly(ethylene glycol) is converted to a carboxylic acid by titration with sodium naphthalene to generate the alkoxide, followed by treatment with bromoethyl acetate to form the ethyl ester, followed by hydrolysis to the corresponding carboxylic acid by treatment with sodium hydroxide and water, as reported by Bückmann et al., *Macromol. Chem.*, 182: 1379–1384 (1981). The resultant carboxylic acid is then converted to a PEG-N-hydroxysuccinimidyl ester suitable for acylation of hGH by reaction of the resultant carboxylic acid with dicyclohexylcarbodiimide and NHS in ethyl acetate.

The resultant NHS-PEG reagent is then reacted with 12 mg/mL of GH using a 30-fold molar excess over GH in a sodium borate buffer, pH 8.5, at room temperature for one hour and applied to a Q Sepharose column in Tris buffer and eluted with a salt gradient. Then it is applied to a second column (phenyl Toyopearl) equilibrated in 0.3M sodium citrate buffer, pH 7.8. The PEGylated hGH is then eluted with a reverse salt gradient, pooled, and buffer-exchanged using a G25 desalting column into a mannitol, glycine, and sodium phosphate buffer at pH 7.4 to obtain a suitable formulated PEG7-hGH.

The PEGylated hGH molecules and hGH-hGH binding protein complex can be characterized by SDS-PAGE, gel filtration, NMR, tryptic mapping, liquid chromatography-mass spectrophotometry, and in vitro biological assay. The extent of PEGylation is suitably first shown by SDS-PAGE and gel filtration and then analyzed by NMR, which has a specific resonance peak for the methylene hydrogens of PEG. The number of PEG groups on each molecule can be calculated from the NMR spectrum or mass spectrometry. Polyacrylamide gel electrophoresis in 10% SDS is appropriately run in 10 mM Tris-HCl pH 8.0, 1 00 mM NaCl as elution buffer. To demonstrate which residue is PEGylated, tryptic mapping can be performed. Thus, PEGylated hGH is digested with trypsin at the protein/enzyme ratio of 100 to 1 in mg basis at 37° C. for 4 hours in 100 mM sodium acetate, 10 mM Tris-HCl, 1 mM calcium chloride, pH 8.3, and acidified to pH<4 to stop digestion before separating on HPLC Nucleosil C-18 (4.6 mm×150 mm, 5µ,100 Å). The chromatogram is compared to that of non-PEGylated starting material. Each peak can then be analyzed by mass spectrometry to verify the size of the fragment in the peak. The fragment(s) that carried PEG groups are usually not retained on the HPLC column after injection and disappear from the chromatograph. Such disappearance from the chromatograph is an indication of PEGylation on that particular fragment that should contain at least one lysine residue. PEGylated hGH may then be assayed for its ability to bind to the hGH binding protein (hGHBP) by conventional methods.

The various PEGylation methods used produced various kinds of PEGylated wild-type hGH, with apparent molecular weights of 35 Kd, 51 Kd, 250 Kd, and 300 Kd by size exclusion chromatography, which should be close to their native hydrodynamic volume. These were designated PEG 1-hGH, PEG2-hGH, PEG3-hGH, and PEG7-hGH, respectively. From the results of the tryptic mapping, the PEG1-hGH and PEG2-hGH both had the N-terminal 9-amino-acid fragment missing from the chromatogram and possibly PEGylated, which could be confirmed by the mass spectrometry of the big molecular species found in the flow-through of the liquid chromatograph. From the molecular weight on SDS-PAGE, PEG 1-hGH may have one PEG on the N-terminal amine, and the PEG2-hGH may have two PEG molecules on the N-terminal amine, forming a tertiary amide. The PEG3-hGH has about 5 PEG groups per molecule based upon the NMR result, and on the tryptic map, at least five peptide fragments were missing, suggesting that they are PEGylated. The PEG7-hGH molecule is believed to have 6–7 PEG groups per molecule based on mass spectrometry.

The sites for adding PEG groups to hGH, and those that are preferred residues for such conjugation, are N-terminal methionine or phenylalanine, lysine 38, lysine 41, lysine 70, lysine 140, lysine 145, lysine 158, and lysine 168. Two lysines that appeared not to be PEGylated were lysine 115 and lysine 172.

The GH is also suitably administered by sustained-release systems. Examples of sustained-release compositions useful herein include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman et al., *Biopolymers*, 22, 547–556 [1983]), poly(2-hydroxyethyl methacrylate) (Langer et al., *J. Biomed. Mater. Res.*, 15: 167–277 [1981], and Langer, *Chem. Tech.*, 12: 98–105 [1982]), ethylene vinyl acetate (Langer et. al., supra) or poly-D-(–)-3-hydroxybutyric acid (EP 133,988), or PLGA microspheres. Sustained-release GH compositions also include liposomally entrapped GH. Liposomes containing GH are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapy. In addition, a biologically active sustained-release formulation can be made from an adduct of the GH covalently bonded to an activated polysaccharide as described in U.S. Pat. No. 4,857,505 issued Aug. 15, 1989. In addition, U.S. Pat. No. 4,837,381 describes a microsphere composition of fat or wax or a mixture thereof and GH for slow release.

The IGF-I may be administered by any means, including injections (single or multiple, e.g., 1–4 per day) or infusions. As with the GH, the IGF-I may be formulated so as to have a continual presence in the blood during the course of treatment, as described above for GH. Thus, it may be covalently attached to a polymer or made into a sustained-release formulation as described above.

In addition, the IGF-I is appropriately administered together with any one or more of its binding proteins, for example, those currently known, i.e., IGFBP-1, IGFBP-2, IGFBP-3, IGFBP-4, IGFBP-5, or IGFBP-6. The IGF-I may also be coupled to a receptor or antibody or antibody fragment for administration. The preferred binding protein for IGF-I herein is IGFBP-3, which is described in WO 89/09268 published Oct. 5, 1989 and by Martin and Baxter, *J. Biol. Chem.*, 261: 8754–8760 (1986). This glycosylated IGFBP-3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-I may be accomplished by the method described in U.S. Pat. No. 5,187,151, the disclosure of which is incorporated herein by reference. Briefly, the IGF-I and IGFBP are administered in effective amounts by subcutaneous bolus injection in a molar ratio of from about 0.5:1 to about 3:1, preferably about 1:1.

Preferably, the administration of both IGF-I and GH is by continuous infusion using, e.g., intravenous or subcutaneous means. More preferably, the administration is subcutaneous for both IGF-I and GH.

The GH in combination with IGF-I to be used in the therapy will be formulated and dosed in a fashion consistent with good medical practice, taking into account the clinical condition of the individual patient (especially the side effects of treatment with GH or IGF-I alone or growth retardation after continuous GH treatment), the site of delivery of the IGF-I and GH composition(s), the method of administration, the scheduling of administration, and other factors known to practitioners. The "effective amounts" of each component for purposes herein are thus determined by such considerations and are amounts that reduce the obesity of a subject over the reduced obesity that is obtained using the same amount of IGF-I or GH individually or prevent obesity or obesity-related conditions from occurring in the first place.

As a general proposition, the total pharmaceutically effective amount of each of the IGF-I and GH administered parenterally per dose will be in the range of about 1 µg/kg/day to 10 mg/kg/day of patient body weight, although, as noted above, this will be subject to a great deal of therapeutic discretion. More preferably, this dose is at least 0.01 mg/kg/day, and most preferably for humans between about 0.01 and 1 mg/kg/day for each hormone. If given continuously, the IGF-I and GH are each typically administered at a dose rate of about 1 µg/kg/hour to about 50/µg/kg/hour, either by 1–4 injections per day or by continuous subcutaneous infusions, for example, using a minipump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner.

It is noted that practitioners devising doses of both IGF-I and GH should take into account the known side effects of treatment with these hormones. For hGH the side effects include sodium retention and expansion of extracellular volume (Ikkos et al., *Acta Endocrinol.* (Copenhagen), 32: 341–361 [1959]; Biglieri et al., *J. Clin. Endocrinol. Metab.*, 21: 361–370 [1961]), as well as hyperinsulinemia and hyperglycemia. The major apparent side effect of IGF-I is hypoglycemia. Guler et al., *Proc. Natl. Acad. Sci. USA*, 86: 2868–2872 (1989). Indeed, the combination of IGF-I and GH may lead to a reduction in the unwanted side effects of both agents (e.g., hypoglycemia for IGF-I and hyperinsulinism for GH) and to a restoration of blood levels of GH the secretion of which is suppressed by IGF-I.

For parenteral administration, in one embodiment, the IGF-I and GH are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I and GH each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or non-ionic surfactants such as polysorbates, poloxamers, or PEG.

The IGF-I and GH are each typically formulated individually in such vehicles at a concentration of about 0.1 mg/ml to 100 mg/ml, preferably 1–10 mg/ml, at a pH of about 4.5 to 8. Full-length IGF-I is generally stable at a pH of no more than about 6; des(1–3)-IGF-I is stable at about 3.2 to 5; hGH is stable at a higher pH of, e.g., 7.4–7.8. It will be understood that use of certain of the foregoing excipients, carriers, or stabilizers will result in the formation of IGF-I or GH salts.

In addition, the IGF-I and GH, preferably the full-length IGF-I, may be formulated together in an appropriate carrier vehicle to form a pharmaceutical composition that preferably does not contain cells. In one embodiment, the buffer used for formulation will depend on whether the composition will be employed immediately upon mixing or stored for later use. If employed immediately after mixing, a mixture of full-length IGF-I and GH can be formulated in mannitol, glycine, and phosphate, pH 7.4. If this mixture is to be stored, it is formulated in a buffer at a pH of about 6, such as citrate, with a surfactant that increases the solubility of the GH at this pH, such as 0.1% polysorbate 20 or poloxamer 188. The final preparation may be a stable liquid or lyophilized solid.

IGF-I and GH to be used for therapeutic administration are preferably sterile. Sterility is readily accomplished by filtration through sterile filtration membranes (e.g., 0.2 micron membranes). Therapeutic IGF-I and GH compositions generally are placed into a container having a sterile access port, for example, an intravenous solution bag or vial having a stopper pierceable by a hypodermic injection needle.

The IGF-I and GH ordinarily will be stored in unit or multi-dose containers, for example, sealed ampoules or vials, as an aqueous solution, or as a lyophilized formulation for reconstitution. As an example of a lyophilized formulation, 10-ml vials are filled with 5 ml of sterile-filtered 1% (w/v) aqueous IGF-I and GH solutions, and the resulting mixture is lyophilized. The infusion solution is prepared by reconstituting the lyophilized IGF-I and GH using bacteriostatic Water-for-Injection.

The GH and IGF-I treatment may occur without, or may be imposed with, a dietary restriction such as a limit in daily food or calorie intake, as is desired for the individual patient.

In addition, the GH and IGF-I are appropriately administered in combination with other treatments for combatting or preventing obesity. Substances useful for this purpose include, e.g., hormones (catecholamines, glucagon, ACTH); clofibrate; halogenate; cinchocaine; chlorpromazine; appetite-suppressing drugs acting on noradrenergic neurotransmitters such as mazindol and derivatives of phenethylamine, e.g., phenylpropanolamine, diethylpropion, phentermine, phendimetrazine, benzphetamine, amphetamine, methamphetamine, and phenmetrazine; drugs acting on serotonin neurotransmitters such as fenfluramine, tryptophan, 5-hydroxytryptophan, fluoxetine, and sertraline; centrally active drugs such as naloxone, neuropeptide-Y, galanin, corticotropin-releasing hormone, and cholecystokinin; a cholinergic agonist such as pyridostigmine; a sphingolipid such as a lysosphingolipid or derivative thereof (EP 321,287 published Jun. 21, 1989); thermogenic drugs such as thyroid hormone; ephedrine; beta-adrenergic agonists; drugs affecting the gastrointestinal tract such as enzyme inhibitors, e.g., tetrahydrolipostatin, indigestible food such as sucrose polyester, and inhibitors of gastric emptying such as threochlorocitric acid or its derivatives; β-adrenergic agonists such as isoproterenol and yohimbine; aminophylline to increase the β-adrenergic-like effects of yohimbine, an $\alpha_2$-adrenergic blocking drug such as clonidine alone or in combination with a growth hormone releasing peptide (U.S. Pat. No. 5,120,713 issued Jun. 9, 1992); drugs that interfere with intestinal absorption such as biguanides such as metformin and phenformin; bulk fillers such as methylcellulose; metabolic blocking drugs such as hydroxycitrate; progesterone; cholecystokinin agonists; small molecules that mimic ketoacids; agonists to corticotropin-releasing hormone; an ergot-related prolactin-inhibiting compound for reducing body fat stores (U.S. Pat. No. 4,783,469 issued Nov. 8, 1988); beta-3-agonists; bromocriptine; antagonists to opioid peptides; antagonists to neuropeptide Y; glucocorticoid receptor antagonists; growth hormone agonists; combinations thereof; etc. This includes all drugs described by Bray and Greenway, *Clinics in Endocrinol. and Metabol.*, 5: 455 (1976).

These adjunctive agents may be administered at the same time as, before, or after the administration of GH and IGF-I and can be administered by the same or a different administration route than the GH and IGF-I are administered.

The invention will be more fully understood by reference to the following examples. They should not, however, be construed as limiting the scope of the invention. All literature and patent citations are expressly incorporated by reference.

EXAMPLE I

Development of New Animal Model of Dietary-Induced Obesity and Investigation of GH Administration Pattern in Lipolytic Weight Reduction Introduction The object of these studies is to develop a new animal model of dietary-induced obesity and to compare the effects of different patterns of GH administration on body composition, specifically on the amount of body fat, in such a model. Recent reviews of the human data (Jorgenson, supra, p. 190) show that GH injections can induce a reduction in whole body fat. However, in man there have been no systematic attempts (similar to the studies to optimize the growth-promoting effects of GH) to define the optimal dose-regimes for the lipolytic actions of GH.

The Dwarf rat (dw/dw) is a recently discovered mutant rat strain that has an isolated lack of pituitary GH, but apparently normal measures of other pituitary hormones. Charlton et al., *J. Endocr.*, 119: 51–58 (1988); Skottner et al., *Endocrinology*, 124: 2519–2526 (1989). Initial interest was to discover if a high-fat diet would cause obesity in the Dwarf (dw/dw) rat. In addition, it was of interest to discover if obesity was then associated with the induction of insulin and/or IGF-I resistance. The obese dw/dw rat might then serve as a model of human disease, especially of Type II diabetes, which is associated with insulin resistance and obesity.

The Dwarf rat (dw/dw) was chosen due to its congenital lack of GH, and because GH deficiency is correlated with obesity in animals and in man. The dw/dw rat is not naturally obese like the classic obese mouse model, the ob/ob. Mayer et al., *Endocrinology*, 52: 54–61 (1953). The dw/dw rat has low blood GH and therefore low blood IGF-I so it is potentially a good animal model to study the effects of GH and IGF-I. Skottner et al., 1989, supra.

Female rats were selected because they maintain a higher body fat percentage and are generally more prone to obesity than male rats. Schemmel et al., *Anat. Rec.*, 166: 437–446 (1969). The traditional diets used routinely to feed laboratory animals are based on grain and are therefore very low in fat (approximately 5% fat by weight). A diet higher in fat (and therefore closer to the human diet eaten in the Western world) was chosen to attempt to induce obesity in the dw/dw rat.

The objects of the present experiments were:

1) To attempt to induce obesity in the dw/dw rat or normal rats by dietary means.

2) To test for insulin resistance in the obese animals.

3) To test the efficacy of GH in reducing body fat in the obese animals.

4) To test the pattern (dose-regime) of GH administration in reducing body fat in the obese animals.

5) To test the effect of dieting (a return from high- to low-fat diet) in combination with different patterns of GH administration, i.e., to test the efficacy of GH during diet-induced weight loss.

Experiments I and II

Methods and Results

Experiment I compared the effect of a high-fat diet on body weight in dw/dw (GH-deficient) and normal (GH-sufficient) rats, and Experiment II confirmed the effect on body weight and obesity of the diet in the dw/dw rats. The degree of obesity was gauged by the mass of selected well defined adipose depot weights, and by the presence of insulin resistance.

EXPERIMENT I:

The first experiment used female rats, 12 Dwarf rats (dw/dw, Simonsen Labs, Gilroy Calif.) and 12 Sprague-Dawley rats (SD, Charles River, Portage). The Dwarf rats had plateaued in body weight (100–140 g) and were 120 days old. The SD rats were weight matched to the Dwarf rats. The SD rats had not plateaued in body weight and weighed 100–140 g and were 40 days old.

The rats were randomized into four groups of six and were weight matched to remove inequalities in mean starting weights. One group of each strain was fed ad libitum for 29 days on normal lab pellets (4.5% fat by weight and 9.6% fat by caloric content). The other two groups were fed an unlimited supply of a high-fat diet (36.3% fat by weight and 56.2% fat by caloric content), also for 29 days. The high-fat diet was made by mixing one part of vegetable shortening with two parts of ground pellets, giving a homogeneous paste. The rats were weighed at least 5 times a week.

During the first experiment, both the SD and the Dwarf rats showed substantial weight gain. Both groups of SD rats increased in body weight throughout the study. But surprisingly, there was no statistical difference in the final body weights of the fat-fed and grain-fed SD rats (Fat-fed, 102.6±20.2 g, Grain-Fed 108.1±18.3 g, t=0.83 by Duncan's Multiple Range test; critical value 2.90). Because the SD rats had not reached their adult or plateaued body weight at the beginning of the experiment, the large weight gain observed was almost certainly the result of normal growth rather than simply an accumulation of adipose tissue.

Both groups of the Dwarf rats also increased in weight throughout the study, but unlike the SD rats there was a clear and consistent difference between the fat- and grain-fed groups of Dwarf rats. This difference was apparent as early as the first day on the different diets (Fat-Fed 3.2±1.7 g, Grain Fed −1.0±3.3 g, t=4.42 by Duncan's Multiple Range test; critical value 2.90) and remained present at 15 days (Fat-Fed 23.3±12.5 g, Grain-Fed 10.4 ±5.3 g, t=4.12 by Duncan's Multiple Range test; critical value 2.90) and at the final 29-day time-point (Fat-Fed 37.0±18.7 g, Grain-Fed 13.3±6.4 g, t=3.7 by Duncan's Multiple Range test; critical value 2.90). Since the body weight of the dwarf rats had plateaued at the beginning of the experiment, their weight gain was most likely due to accumulation of adipose tissue.

EXPERIMENT II:

In the second experiment, there were four groups of six Dwarf rats each, to repeat and confirm the above findings and to measure insulin sensitivity and adipose mass, Again, the fat-fed rats began to gain weight immediately. After being fed the diets for 28 days, the fat-fed rats were substantially (p<0.001) heavier (155.7±6.2 g) than the grain-fed rats (128.4±11.5 g) . After 7 days on the different diets half the rats were subjected to an insulin tolerance test using an i.v. injection of insulin (0.4 u/kg). At this time there was no difference between the blood glucose responses of the two groups.

Both fat and lean rats were also given an i.v. injection of insulin (0.4 u/kg) at 28 days as an insulin tolerance test. Blood was sampled before and after the injection for measurement of blood glucose. The blood glucose of the grain-fed animals showed a large decrease after the insulin injection, from an initial level of 162.7±22 mg % to 94.0±25.0 mg % or 56.9% of initial after 20 minutes. The maximum drop in blood glucose was at 20 minutes and levels began to rise at 40 minutes. The fat-fed animals were resistant to this dose of insulin. Their blood glucose concentrations only dropped to 89.4±2% of the initial concentration (210±23 mg %), with a maximum drop at the 20-minute time point. These responses to insulin were statistically different between the groups, demonstrating that clear insulin resistance was induced in the fat-fed rats at 28 but not at 7 days on the diets. Therefore, the insulin resistance did not seem to depend on the diet, but rather on the development of obesity.

Obesity was measured directly after the animals were sacrificed (after 29 days of high- or low-fat diets); the parametrial and retroperitoneal fat pads were dissected, weighed, and compared between the groups. The fat pads of the fat-fed animals were significantly larger than the fat pads of the grain-fed animals. The mean parametrial fat pad weights (mean±SD) were 2.3±0.6 g for the grain-fed animals and 5.2±1.4 g for the fat-fed animals. One-way analysis of variance for these figures gave an F value of 25.57 with $1/14$ degrees of freedom, a highly significant difference ($P<0.001$). Likewise, the mean retroperitoneal fat pad weights were 0.9±0.4 g for the grain-fed animals and 2.39±0.7 g for the fat-fed animals. One-way analysis of variance gave an F value of 24.67 with $1/14$ degrees of freedom for this measurement, again very different statistically.

Discussion of Exps. 1 & 2

The intention of the first experiment was to compare the Dwarf rats to the SD rats for their tendency to develop obesity. The Dwarf rats clearly became obese; the SD rats did not. Presumably, the normal endogenous levels of GH in the SD rats prevented obesity, and the low levels in the dw/dw rats allowed obesity. One would therefore expect that treating rats prophylactically with GH would prevent the occurrence of obesity.

The object of the second experiment was to show that obese dw/dw rats became insulin resistant with time due to the development of obesity.

For the high-fat diet, the caloric fat content was chosen to be 56% because this seemed to be a reasonable maximum. A higher level would be likely to result in protein malnutrition due to a lack of ample protein in the diet. Also, the consistency of the diet at a 1:2 fat to grain ratio gave a mixture that was easy to prepare and feed.

The above studies clearly demonstrated that GH deficiency made the animals prone to develop obesity. The next set of experiments investigated how GH could reverse this obesity.

Experiments III and IV

Background

Before the effect of different GH treatment regimens was tested in obese dw/dw rats, the effects of these treatments were measured in non-obese dw/dw rats. The first study used young female dw/dw rats; the second study used older, mature male dw/dw rats.

Young Female Rats

Figure 2:
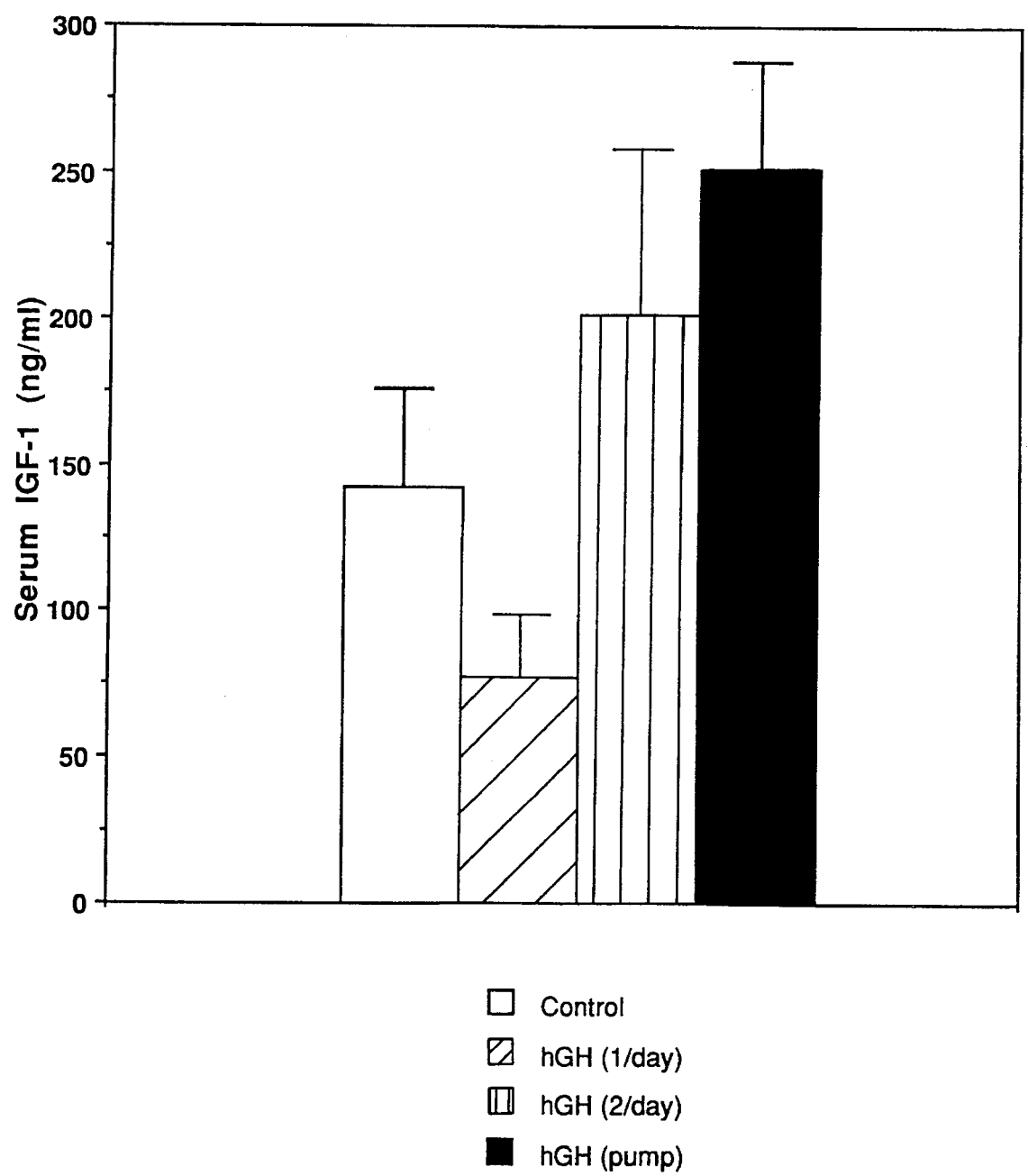
FIG. 2 shows the serum IGF-I levels after 8 days of treatment for the rats treated as described in FIG. 1, where the key is given in the legend for FIG. 1.

In young (6–9 week old) non-obese dw/dw female rats the pattern of GH administration determines the anabolic response to GH. FIG. 1 shows the body weight gain over 8 days in such rats (n=5/group) given NUTROPIN® brand recombinant hGH (5-mg vial, at 2 mg/ml in 18 mg/ml mannitol, 0.68 mg/ml glycine, and 5 mM phosphate, pH 7.4) at a dose of 240 µg/day, s.c. in three different regimes, or given hGH excipient (the mannitol buffer without hGH). For a given dose of GH, the GH given as two injections per day had the largest anabolic effect, continuous infusions being the next most effective treatment, with daily injections having the smallest anabolic effect. The serum IGF-I levels in these young rats (FIG. 2) taken 24 hours (once daily injections) or 16 hours (twice daily injections) after the last GH injection were either depressed (daily injection) or increased (twice daily injection and mini-pump infusion).

Therefore, the largest weight gains (FIG. 1) were obtained with infusions or twice daily injections of GH and were accompanied by increases in serum IGF-I.

Mature Male Rats

Much older 30-week-old male dw/dw rats were employed to test the effect of the pattern of hGH administration on body weight gain and fat depot weight. In the rat sexual maturity occurs at 5–6 weeks and body weight plateaus at about 15 weeks of age, so by 30 weeks a rat has reached sexual maturity, and has attained adult body proportions. A 30-week-old male rat also has larger stores of body fat than a rat 8–10 weeks of age. Therefore, three groups of 30-week-old male dw/dw rats were given hGH (NUTROPIN® brand hGH, 5-mg vial), either by daily injection or by mini-pump, or given hGH excipient. All the rats were fed a standard pelleted low-fat grain diet. There was no evidence that the treatments affected food intake in these young or older non-obese rats.

The results (Tables I and II) in these older grain-fed non-obese male rats were similar to those in the young rats, i.e., the infusion of GH caused a larger weight gain than daily injections of GH (particularly at early time points after the beginning of the infusion). The fat depots (epididymal and retroperitoneal) were not significantly affected by the GH treatments. The average depot weights were in fact numerically increased in weight by GH treatment, but statistical significance was not achieved. See U.S. Pat. No. 5,126,324, supra.

Therefore, in mature but non-obese animals fed a low-fat diet, GH caused weight gain, with no change in adipose tissue mass, when given by injection or infusion, with both patterns of GH administration causing weight gain, and no differential effect on body composition was observed.

In addition, Table II shows that GH infusions increased serum GHBP and IGF-I concentrations, compared to GH injections. Serum glucose was unchanged but serum cholesterol and triglyceride concentrations were greatly increased by GH infusion compared to control or GH-injected animals.

TABLE I

Growth Parameters in Adult Male dw/dw Rats:
Treated with Excipient,
hGH (500 µg, s.c.) by Daily Injection,
or by Infusion

| Group | Body Weight Gain (Day 4) (g) | Body Weight Gain (Day 14) (g) | Retro-peritoneal Fat Weight (g) | Epipdi-dymal Fat Weight (g) |
|---|---|---|---|---|
| Excipient | −7.8 ± 5.6 | −3.7 ± 2.5 | 3.1 ± 1.2 | 2.6 ± 1.0 |
| hGH Injection | 4.0 ± 3.4 | 28.1 ± 9.2 | 3.5 ± 1.8 | 2.9 ± 1.1 |
| hGH Infusion | 12.9 ± 4.4* | 31.2 ± 13.0 | 4.0 ± 1.8 | 3.3 ± 1.2 |

TABLE II

Blood Parameters in Adult Male dw/dw Rats:
Treated with Excipient,
hGH (500 µg, s.c.) by Daily Injection,
or by Infusion

| Group | Serum IGF-I (ng/ml) | Serum GHBP (ng/ml) | Serum Glucose (mg/dl) | Serum Cholesterol (mg/dl) | Serum Triglyceride (mg/dl) |
|---|---|---|---|---|---|
| Excipient | 154 ± 43 | 11 ± 1 | 130 ± 9 | 75 ± 8 | 118 ± 19 |
| hGH Injection | 202 ± 31 | 14 ± 3 | 130 ± 5 | 83 ± 10 | 119 ± 25 |
| hGH Infusion | 285 ± 41* | 78 ± 17* | 134 ± 6 | 133 ± 27* | 185 ± 47* |

Values in both Tables are Means ± SDs, n = 7–8/group.
p < 0.05 vs. hGH by Injection.

Introduction

In the next two studies (Experiments III and IV) female dw/dw rats were fed a high-fat diet for 8 weeks. It appeared that the high-fat diet induced an initial rapid weight gain; the fat-fed rats then settled into a stable but obese body composition. This conclusion was reached from the relatively modest weight gain between 6 and 8 weeks on the high-fat diet, rather than by detailed body compositional analysis. For these studies it is assumed that studying stable obese animals, rather than animals in a dynamic phase of increasing obesity, might reflect the common human situation of long-term stable obesity (where the lipolytic effect of GH treatment would be expected to be commonly used).

Therefore, in two subsequent studies rats were made obese and then treated with hGH to study its effect on body weight gain, organ weights and adipose depot size. The pattern of GH administration was investigated to determine if it was an important factor in determining the lipolytic activity of GH.

In the initial study in obese dw/dw rats GH was given as an infusion or by one or two injections a day. It was hypothesized that, as for the anabolic effect of GH, the lipolytic effects of the different patterns of GH would have a similar relative effectiveness, i.e., that two injections of GH per day would be more effective than infused GH, which would be more effective than one injection of GH per day. The second study attempted to duplicate the initial study (treating the rats with GH and maintaining the high-fat diet) and also to test the effects of concurrent "dieting" (returning the rats to a low-fat diet) and GH- treatment regimes.

EXPERIMENT III

Sixty female dw/dw rats (105–150 g, 90 days of age) were group housed and fed ad libitum a high-fat diet for 8 weeks, with water also available ad libitum. After 8 weeks on the diet the heaviest (most obese) 40 rats (average weight 185 g) were chosen for subsequent use. The rats were then anesthetized (with ketamine/xylazine, i.p.) and two osmotic ALZA® mini-pumps (2002, pump rate 0.46 µl/hr, Alza Corporation, Palo Alto, Calif.) were inserted subcutaneously. The pumps were filled with either recombinant hGH (5 mg/vial, NUTROPIN® brand) or hGH excipient. The hGH was diluted to 22.6 mg/ml so that 2 pumps would deliver 22 µl/day times 22.6 µg/µl or approximately 500 µg/day of hGH. For the injections of hGH, solutions of 5 mg/ml and 2.5 mg/ml of hGH were prepared, so 100µl of the 5 mg/ml solution could be injected daily (500 µg/day) or 100 µl of the 2.5 mg/ml solution could be injected twice daily (2 times 250 µg, also giving a dose of 500 µg/day).

The treatments were continued for 14 days when the rats were sacrificed (n=10/group):

1) excipient pumps, excipient injections
2) hGH pumps, excipient injections
3) excipient pumps, one hGH injection (500 µg)/day
4) excipient pumps, two hGH injections (2>250 µg)/day

EXPERIMENT IV

Female dw/dw 70 days of age were group housed and fed a high- fat diet ad libitum for 7 weeks, with water also available ad libitum. A separate group of 10 rats were maintained on their original grain diet. After 7 weeks on the high-fat diet the heaviest (most obese) 42 rats were chosen for subsequent use. The rats were then anesthetized (with ketamine/xylazine, i.p.) and an osmotic ALZA® mini-pump (2ML2, pump rate 5.12 µl/hr, Alza Corporation, Palo Alto, Calif.) was inserted subcutaneously. The pumps were filled with either recombinant hGH (5 mg/vial, NUTROPIN® brand) or hGH excipient. The hGH was diluted to 4.1 mg/ml. The 2ML2 pump delivered 5.12 µl/hr or 5.12 times 24=122.88 µl/day, so with hGH at 4.1/µg/µl the amount of hGH delivered was 122.88 times 4.12=approximately 500 µg/day. For the injections of hGH a solution of 5 mg/ml hGH was prepared, so 100 µl of the 5 mg/ml solution could be injected daily (500 µg/day).

The treatments were for 14 days (n=7/group):
High-fat diet for 7 weeks, and high-fat diet continued 1) excipient pumps, excipient injections
2) hGH pumps, excipient injections
3) excipient pumps, one hGH injection/day High-fat diet for 7 weeks, and then switched to a low-fat (grain) diet 4) excipient pumps, excipient injections
5) hGH pumps, excipient injections
6) excipient pumps, one hGH injection/day Grain diet for 7 weeks, continued on a grain diet 7) excipient pumps, excipient injections Sacrifice and autopsy occurred after 14 days, when body organs, including fat pads, were removed and weighed and blood was taken for the measurement of metabolites and hormones.

Results of Exps. III and IV

Experiment III

Figure 3:
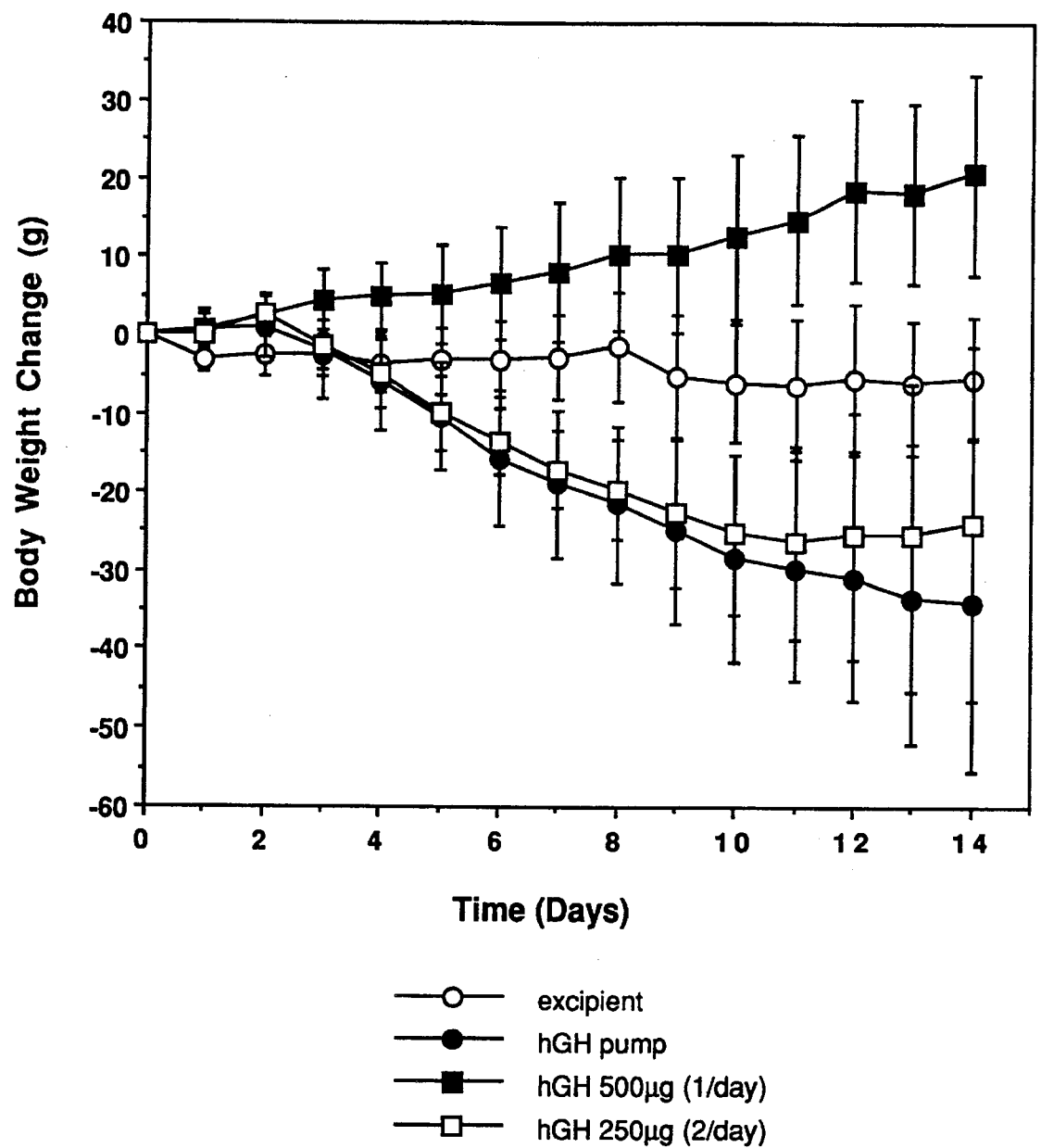
FIG. 3 shows the daily cumulative body weight gains in obese dw/dw rats over a 14-day treatment period. The open circles are excipient, the solid circles are hGH pump, the solid squares are hGH 500 μg once per day, and the open squares are hGH 250 μg twice daily.
Figure 4:
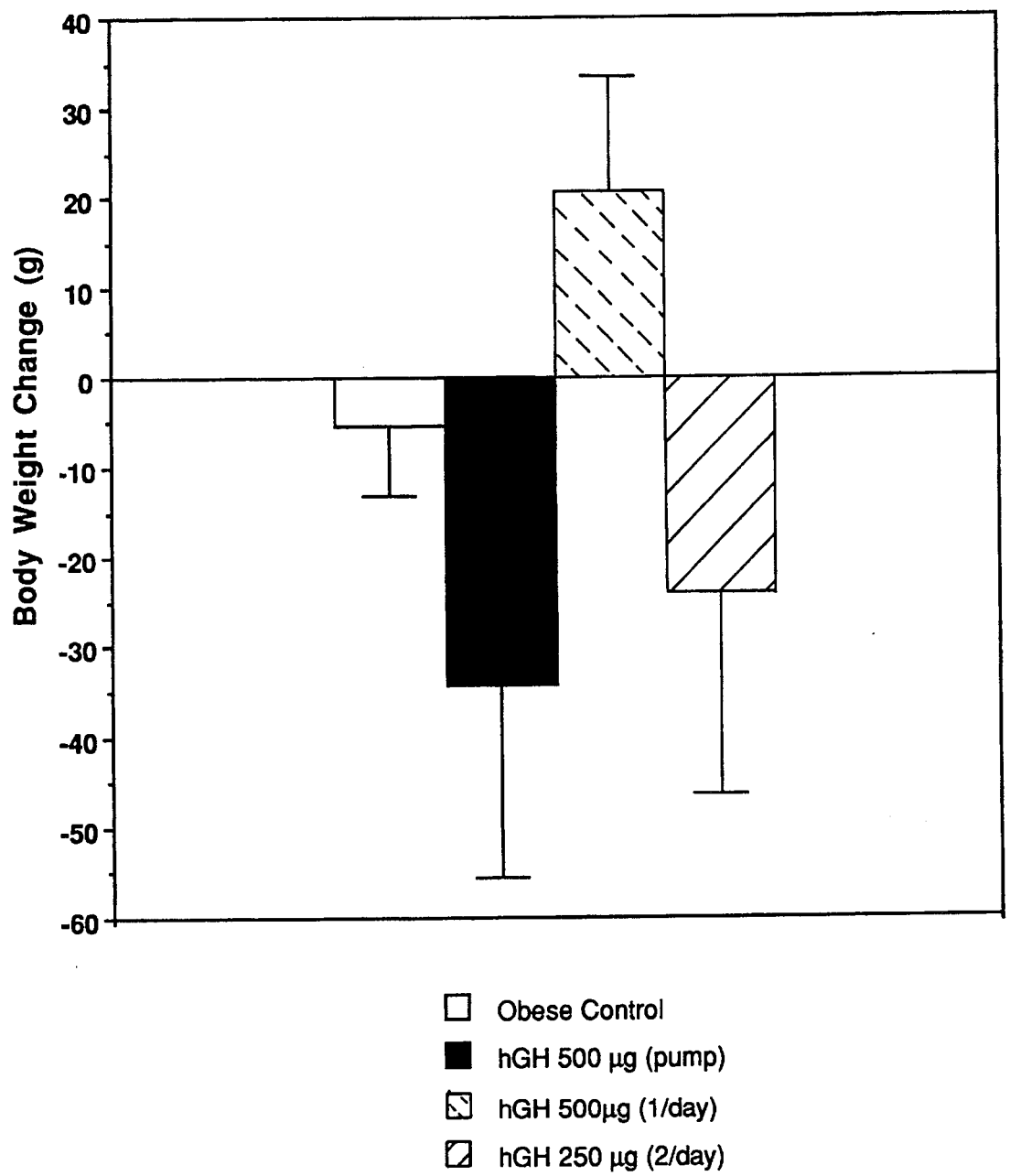
FIG. 4 shows the final weight gains in obese dw/dw rats after 14 days of treatment, where the open bars are excipient, the solid bars are hGH 500 μg by pump, the shaded bars are hGH once per day, and the diagonal lines are hGH 250 μg twice daily.

FIGS. 3 and 4 and Table III show the weight gains in obese dw/dw rats over 14 days. FIG. 3 shows the gains with time; FIG. 4 and Table III show the final gains. Statistically significant effects are shown in Table III. The excipient-treated rats maintained their body weight (−5 g); if rats were treated with daily GH injections they gained weight (21 g). But if GH was given by infusion or by twice daily injections, weight loss occurred (−34 or −24 g, respectively). These clear differences in the body weight response to different patterns of GH administration were unexpected. In particular, the loss in body weight upon GH treatment was opposite to the expected results shown in FIG. 1 and Table I.

Figure 5:
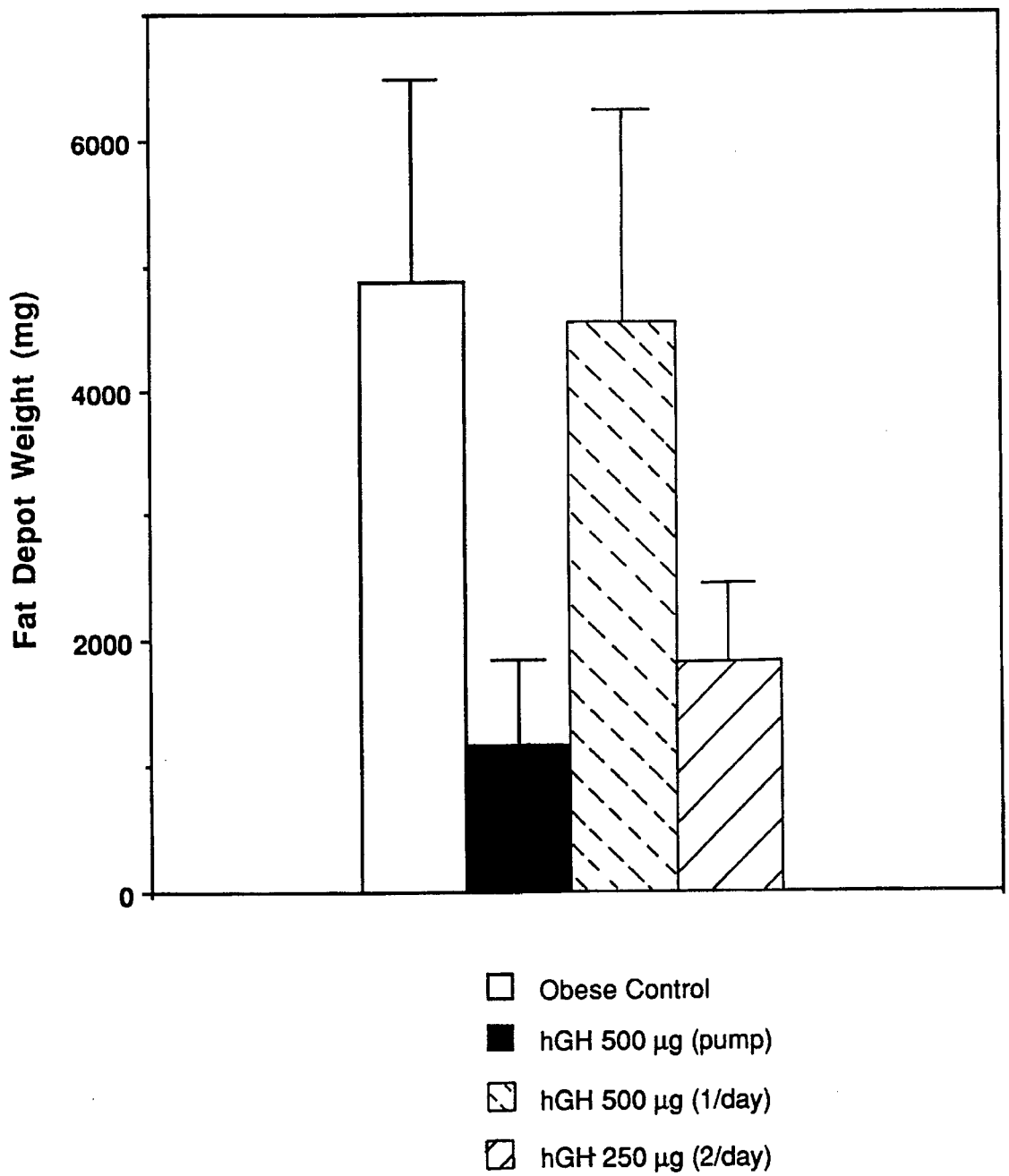
FIG. 5 shows the weight of the retroperitoneal fat pad after 14 days of treatment in obese dw/dw rats, where the bars are as described for FIG. 4 above.

The retroperitoneal fat pad weight in the dw/dw rats is shown in FIG. 5 and Table III. GH given by daily injection for 14 days at 500 μg/day/rat did not significantly reduce body fat in either the retroperitoneal, mesenteric, or ovarian/gonadal depots, but if rats were treated with GH by infusion or two injections of GH per day, fat loss occurred in all three depots (Table III). This dramatic loss in body fat was again different from the results shown in Table I in non-obese rats. Therefore, the body fat depot changes showed the same trend as did the body weight changes in response to different patterns of GH administration in the obese dw/dw rat.

The serum IGF-I, GHBP, glucose, cholesterol, and triglyceride levels in dw/dw rats at sacrifice are shown in Table IV. Serum IGF-I levels in the obese rats were increased by daily GH injection but unchanged by infusions or twice daily injections of GH. Serum GHBP was unchanged by treatment. Compared to daily injections of GH, GH infusions or twice daily injections of GH had different effects on serum glucose and triglyceride concentrations.

It is instructive to compare GH treatment in non-obese dw/dw rats (Tables I and II) with GH treatment in obese dw/dw rats (Tables III and IV). In non-obese rats (Table I), GH, irrespective of delivery pattern, increased weight gain and had no effect on body fat stores. In obese rats (Table III) either weight gain or weight loss was observed. In non-obese rats, hGH infusion increased IGF-I, GHBP, cholesterol, and triglyceride levels compared to hGH injection (Table II). But in obese rats IGF-I and glucose levels were decreased by GH infusion compared to GH injection, and no rise in GHBP, cholesterol, or triglyceride levels occurred (Table IV). It is very clear that different hGH regimes have very different effects on many measurements in non-obese and obese rats.

TABLE III

Growth Parameters in Obese Fat-Fed Female dw/dw Rats
Treated with: Excipient, hGH (500 μg, s.c.) by either Infusion
or Once or Twice Daily Injections

| Group | Body Weight Gain (Day 14) (g) | Retro-peritoneal Fat Weight (g) | Mesenteric Fat Weight (g) | Ovarian Fat Weight (g) |
|---|---|---|---|---|
| Excipient | −5 ± 8 | 4.9 ± 1.6 | 2.5 ± 0.9 | 4.5 ± 2.0 |
| hGH Infusion | −34 ± 21* | 1.1 ± 0.7* | 1.6 ± 0.9* | 2.1 ± 1.1* |
| hGH (1/day) Injection | 21 ± 13 | 4.5 ± 1.7 | 2.8 ± 0.9 | 4.6 ± 2.1 |
| hGH (2/day) Injection | −24 ± 22* | 1.8 ± 0.6* | 2.1 ± 0.9 | 2.6 ± 1.0* |

TABLE IV

Blood Parameters in Obese Fat-Fed Female dw/dw Rats:
Treated with Excipient, hGH (500 μg, s.c.)
by Either Infusion or Once or Twice Daily Injections

| Group | Serum IGF-I (ng/ml) | Serum GHBP (ng/ml) | Serum Glucose (mg/dl) | Serum Cholesterol (mg/dl) | Serum Triglyceride (mg/dl) |
|---|---|---|---|---|---|
| Excipient | 143 ± 24 | 14 ± 4 | 158 ± 27 | 82 ± 13 | 93 ± 30 |
| hGH Infusion | 124 ± 721 | 16 ± 9 | 93 ± 30* | 73 ± 22 | 90 ± 43* |
| hGH (1 /day) Injection | 210 ± 66 | 17 ± 13 | 164 ± 29 | 76 ± 6 | 130 ± 18 |
| hGH (2/day) Injection | 103 ± 58* | 10 ± 3 | 138 ± 21* | 88 ± 19 | 118 ± 28 |

Values in both Tables are Means ± SDs, n = 10/group.
*p < 0.05 vs. hGH by injection.

Experiment IV

Figure 6:
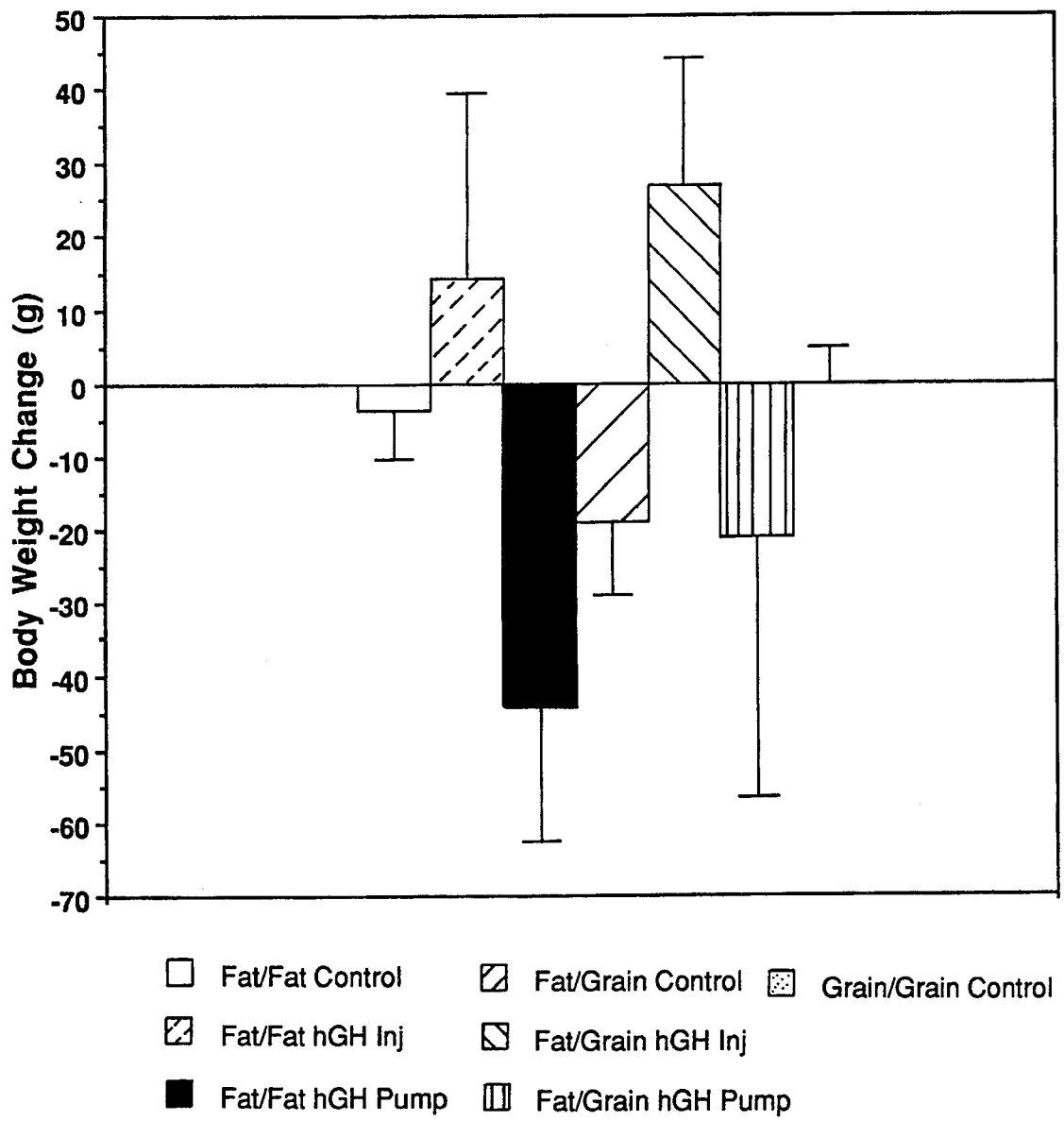
FIG. 6 shows the body weight change in female dw/dw rats after 14 days of treatment. The groups of rats were: fat/fat control (open bars), fat/fat hGH injection (shading on left), fat/fat hGH pump (solid), fat/grain control (wide diagonals), fat/grain hGH injection (medium diagonals), fat/grain hGH pump (narrow diagonals), and grain/grain control (shading on right).

FIG. 6 shows the cumulative weight gains in dw/dw rats after 14 days. The first three groups (fat/fat) were fed a high-fat diet throughout; the second three groups were changed from high fat to grain at the time GH treatment was begun (fat/grain), and the seventh group (grain/grain) was fed grain throughout. GH was given by daily injection or mini-pump infusion for 14 days at 500/μg/day/rat. The rats fed high fat or grain throughout maintained their body weight over the 14 days, but if the fat-fed rats were switched to a grain diet they lost weight (as expected). If rats were treated with daily GH injections they gained weight, irrespective of diet. Therefore, the effect of dieting from a high-fat to a grain diet was lost if GH was given by injection. But if GH was given by infusion weight loss occurred irrespective of diet.

On the fat/fat diet, GH-injected rats gained body weight (14±25 g), whereas GH-infused rats lost weight (−44±18 g, $p<0.001$ vs. GH-injected). On the fat/grain diet GH-injected rats again gained weight (27±17 g), and GH-infused rats lost weight (−21±36 g, $p <0.01$ vs. GH-injected). Once again, there are clear differences in the body weight response to different patterns of GH administration in the obese rat, even when dieting occurs.

Figure 7:
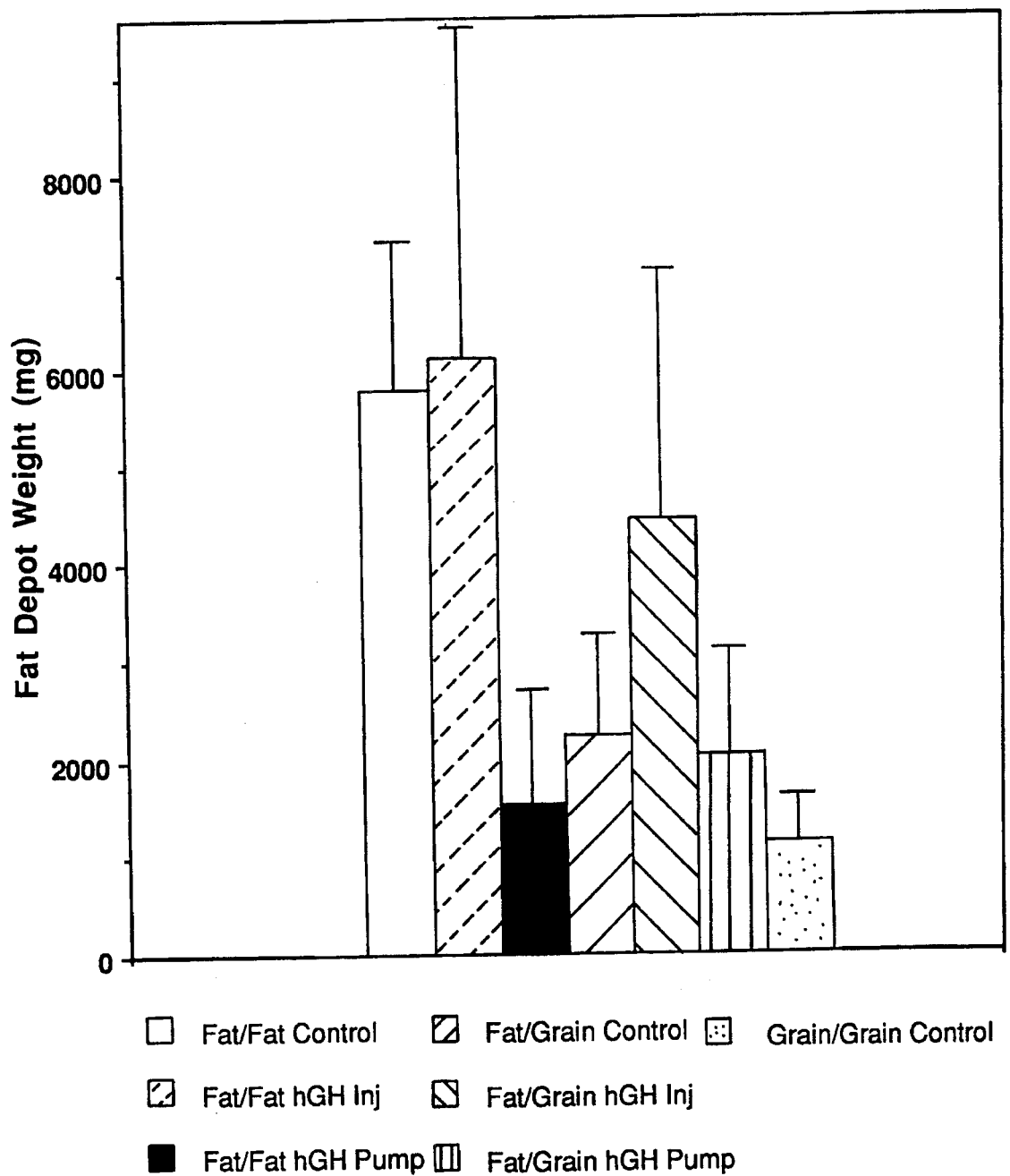
FIG. 7 shows the retroperitoneal fat depot weight in dw/dw rats after 14 days of treatment, where the key is described in the legend for FIG. 6.

FIG. 7 shows the retroperitoneal fat pad weight in dw/dw rats. The obesity of the fat-fed rats can be seen by comparing bars 1 and 7; the fat-fed rat depots average 5806 mg while the grain-fed depots averaged 1137 mg (a 5-fold difference in adiposity). The responses to GH treatment were particularly surprising. GH given by daily injection for 14 days at 500 μg/day/rat did not significantly reduce body fat, but if rats were treated with GH by infusion, statistically significant fat loss occurred irrespective of diet.

On the fat/fat diet the retroperitoneal pad weights of GH-injected rats (6110±3400 mg) were larger ($p<0.001$) than the pad weights of fat/fat GH-infused rats (1542±1168 mg). On the fat/grain diet the retroperitoneal pad weights of GH-injected rats (4444±2570 mg) were again larger ($p<0.05$) than the pad weights of fat/grain GH-infused rats (2040±1075 mg). As for the body weight changes, there were clear differences in body fat responses to different patterns of GH administration in the obese rat.

Conclusion

A primary conclusion from these studies is that the effects of GH on body composition are surprisingly dependent on the pattern of GH administration. These studies predict that in man only the continuous presence of GH in the blood would be effective in reducing body fat, as achieved by, for example, frequent (twice daily or more) injections of GH, as well as continuous infusion or other methods of prolonging the presence of GH in the blood to produce weight loss in an obese human (including encapsulating GH in a sustained-release formulation, attaching a polymer to the GH to make it long-acting, or administering the GH bound to a binding protein thereof).

The large serum IGF-I response to GH infusion seen in non-obese rats was absent in the obese rats. In addition, the serum GHBP levels were not increased by GH infusion. Therefore, there appears to be a degree of GH resistance (using IGF-I and serum GHBP as markers) in the obese rat when GH is given continually. However, the lipolytic response to GH shows that GH resistance is not global.

These studies are the first, to applicant's knowledge, of feeding high-fat diets to rats with hereditary GH deficiency (GHD). Humans with GHD have an altered body composition, with increased body fat contents. Rudman, *J. Amer. Geriatr. Soc.*, 33: 800–807 (1985). The dietary obese female (dw/dw) rat gives an interesting model for GH deficiency somewhat akin to an obese human GHD. It should also be noted that with age humans become GH deficient (see Rudman, [1985], supra, p. 804), so it is reasonable to assume that the rodent model used herein may also be close to that of an overweight human who is GH deficient. It is unclear if obesity in humans is associated with both a relative GH deficiency (due to reduced GH secretion) or a relative lack of GH responsiveness (reduced GH receptors or GH receptor coupling). It is shown herein that an animal with a genetic propensity to become obese can rapidly lose weight by appropriate GH treatment. One would assume that other mammals that have a genetic makeup that causes them to become obese would also respond to appropriate GH treatment with a loss of body fat.

EXAMPLE II

Investigation of Different GH Administration Patterns in Lipolytic Weight Reduction Introduction This study was conducted to discover if different patterns of hGH administration affect food intake in obese female dw/dw rats.

Methods

Ninety-five 12 to 16 week old female dw/dw rats (Simonsen Labs, Gilroy, Calif.) were placed on a high-fat diet consisting of one part CRISCO™ vegetable shortening to 2 parts PURINA® powdered rodent chow. Rats remained on this high-fat diet for a total of 11 weeks until this study was begun. Fifty-four rats were placed on the study described in Example III below. From the remaining animals the 23 rats that gained the most weight were used in the present study.

On day −3 before initial treatment (day 0) the rats were placed on the powdered rodent chow and placed in NALGE metabolic cages to acclimate them before treatment. Lean controls were not used in this study. On day 0 rats were anesthetized using Ketamine/Xylazine i.p. (125:25 mg/kg), a subcutaneous incision was made dorsally, and one ALZA™ 2002 osmotic mini-pump (Alza Corporation, Palo Alto, Calif.) containing either hGH or excipient was placed subcutaneously. A second group of rats were injected subcutaneously with either hGH or excipient, recovered on a heated pad until ambulatory, and then placed in their home cage. Rats were thereafter injected daily, weighed daily, and sacrificed on day 14.

| Groups were as follows:* | | | |
|---|---|---|---|
| Group | Injections | Pump | |
| 1 | excipient | excipient | N = 7 |
| 2 | hGH 300 μg | excipient | N = 7 |
| 3 | excipient | hGH 300 μg | N = 8 |

*Dosages are daily totals.

The reagents employed were NUTROPIN® brand hGH, 5-mg vial, and hGH excipient (the buffer used in NUTROPIN® brand hGH, 5 mg/ml equivalent).

On day 15 the rats were sacrificed using $CO_2$, and serum and fat depots were collected for further analysis and wet weights.

Results

Figure 8:
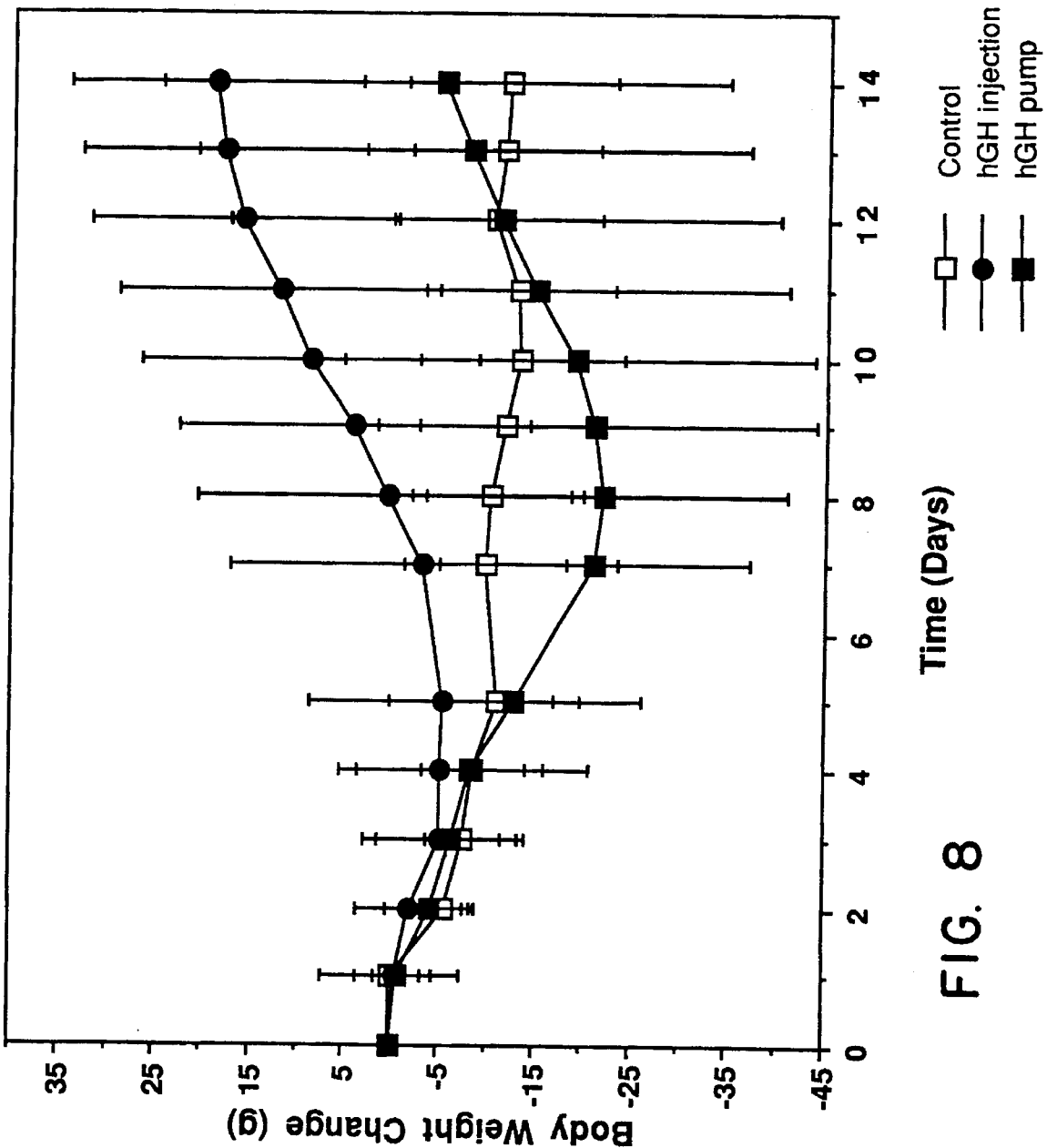
FIG. 8 shows the cumulative body weight changes in obese female dw/dw rats over 14 days of treatment. The groups were control (open squares), hGH by daily injection (solid circles), or hGH infusion by mini-pump (solid squares).

Body Weight:
All rats were transferred to a grain diet on day −3 when they were placed in metabolic cages, which could explain weight loss in the control animals. The change in body weight as shown in FIG. 8 appeared uniform up to day 5. At this point, rats receiving hGH injections began to gain weight and those receiving infusions began to lose weight.

The group of animals receiving GH infusions lost weight until about day 9 and then began to regain weight. On day 14 control rats had lost weight (−12±11 g). Once again GH injection caused weight gain (18.8±15 g) compared to the weight loss of GH-infused rats (−5±30 g, p<0.05 vs. GH injection).

Figure 9:
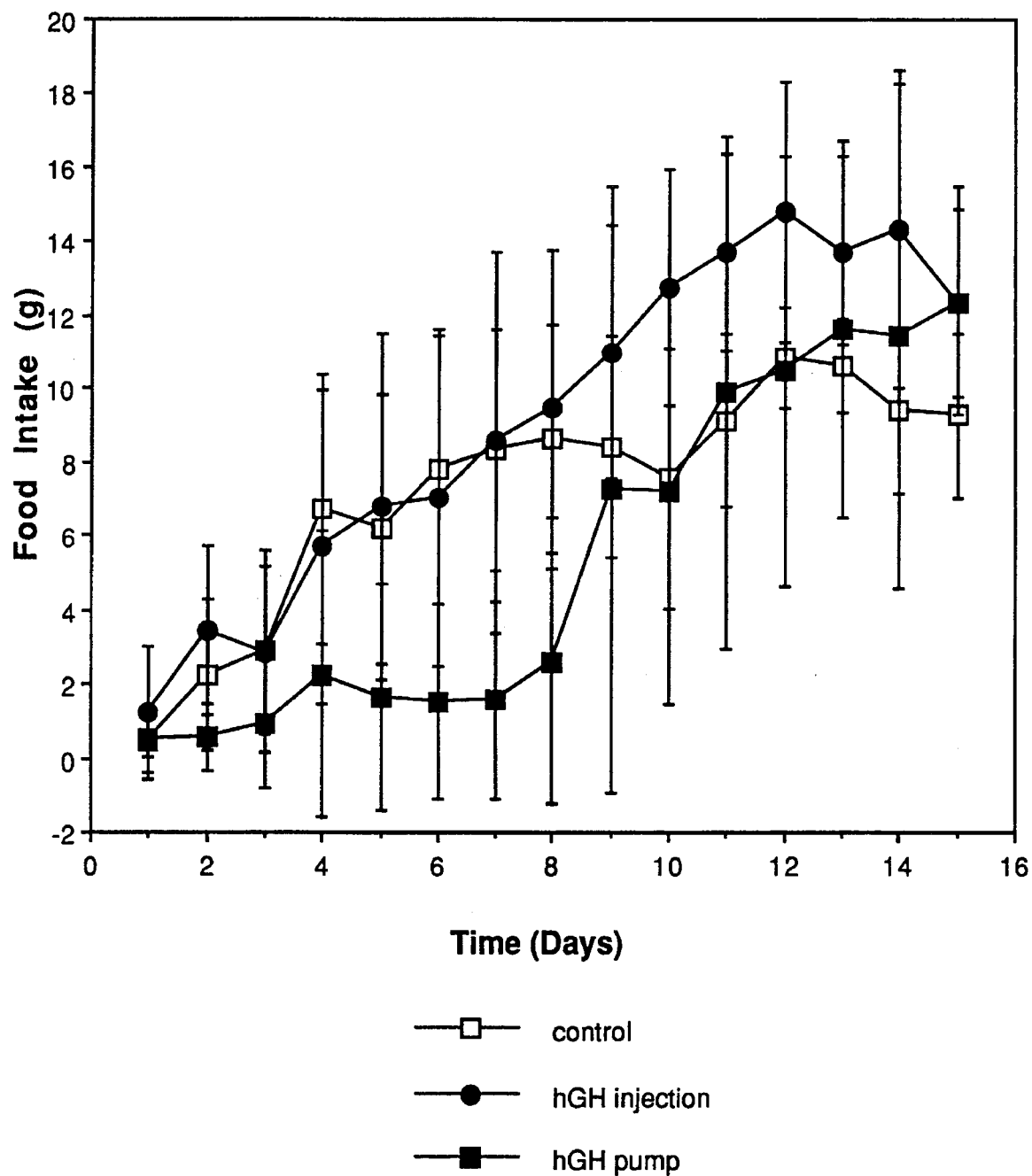
FIG. 9 shows the daily food intakes of obese female dw/dw rats over 14 days of treatment, wherein the key is explained in the legend to FIG. 8.

Food Intake:

Food intake of the infusion group as shown in FIG. 9 appeared to parallel that of body weight changes in that the animals appeared to eat dramatically less than the injection and control groups until day 8. On day 8 control rats ate 8.6±31 g. GH-injected rats ate significantly (p<0.05) more food (9.4±4.3 g) than GH-infused rats (2.6±3.8 g). At this point GH-infused rats began to eat and by day 15 were eating amounts equal to that of the injection group. There was therefore a clear difference between the two regimes of hGH treatment in the obese rats; hGH given by infusion reduced food intake, while hGH given by daily injection tended to increase food intake.

Figure 10:
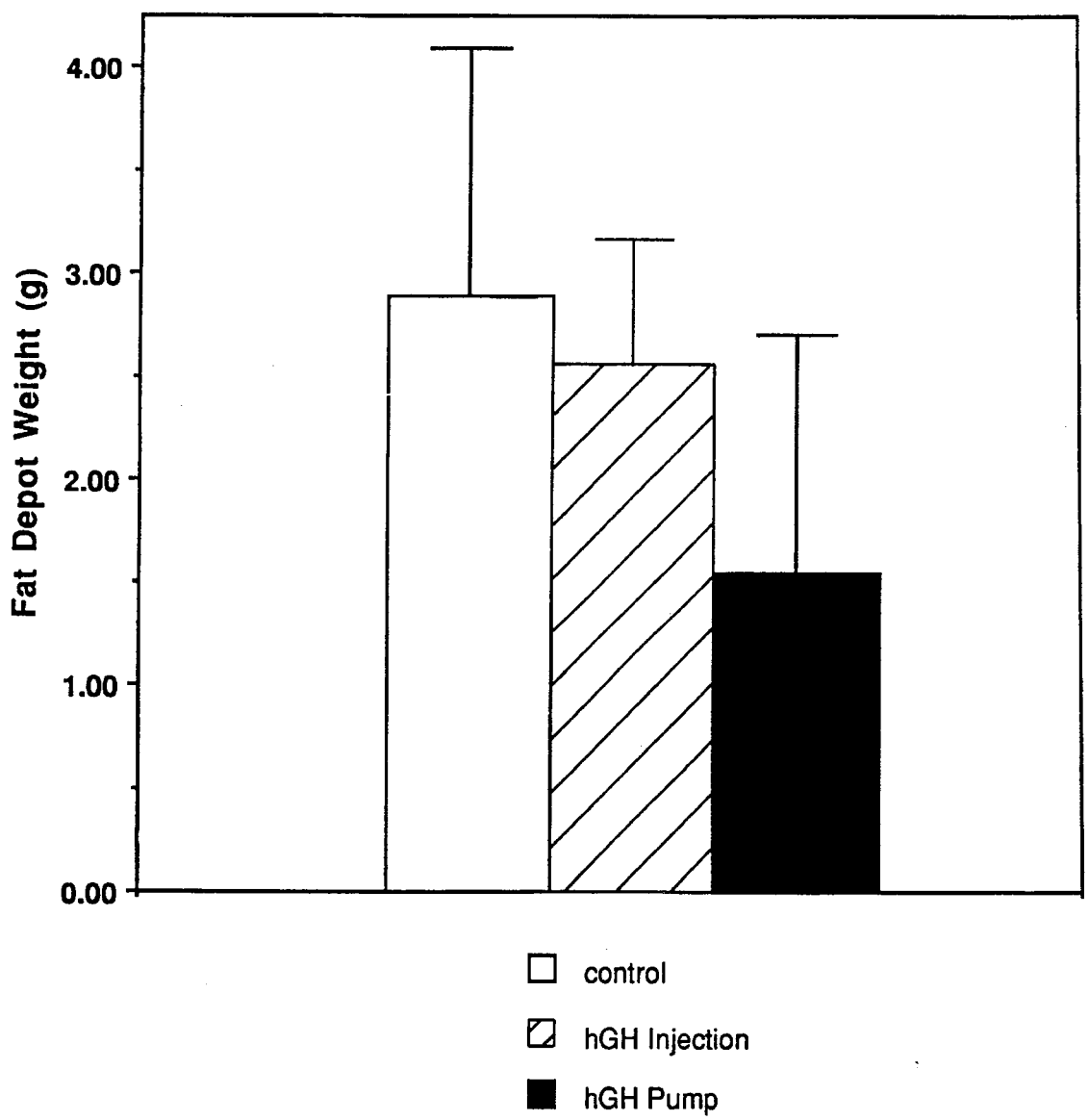
FIG. 10 shows the fat depot weight in grams of obese female dw/dw rats after 14 days of treatment. The weight groups were control (open bars), hGH by daily injection (diagonal lines), or hGH infusion by mini-pump (solid bars).

Fat Depots:

The fat depot weights shown in FIG. 10 indicate that the weight loss from GH infusions is likely to be due to a loss of fat. Fat pad weights in control rats (2.9±12 g) were significantly larger (p<0.05) than those from GH-infused rats (1.5±1.2 g), but not from GH-injected rats (2.6±0.6 g).

Physical Appearance:

Rats receiving hGH infusions lost weight quickly, and decreased their eating, drinking, urinating, and defecating for a number of days. It seemed that some rats were affected more than others, but there was no obvious correlation between the degree of initial obesity or body weight and the degree of reduction in appetite or weight loss.

Conclusion

The body weight data show that the pattern of hGH delivery strongly affects body weight gain, fat depots, and food intake. Daily hGH injections caused weight gain, and hGH infusions caused weight loss. Also, hGH infusion caused a reduction in food intake until body weight and/or body fat stores reached a new level where food intake resumed. The amount of food intake of the infusion animals was statistically less up to day 8. At this point GH-infused animals began to eat and by day 15 were equal in food intake to that of the daily injection group and not statistically different from that of control. This same pattern was seen in the weight gain data.

In contrast to the reduced food intake in the rats given GH infusions, the rats given GH injections showed no change in food intake, compared to control (excipient-treated) rats. Once again, fat depots were reduced by GH infusion, but not by GH injection. In summary, GH infusions caused weight loss, anorexia, and a loss of body fat, whereas (at the same dose of GH) daily injections of GH increased body weight and did not affect food intake or body fat stores.

EXAMPLE III

Use of GH, IGF-I, or GH and IGF-I to Treat Obese Rats

Introduction

This study was conducted to confirm the effects of different patterns of GH administration and to study their dose dependence. In addition, the study was performed to discover the effects of the administration of IGF-I alone or its co-administration with GH on carcass composition, whole body and organ weights, serum chemistries, and endocrine hormone levels in obese dw/dw rats.

Methods

Dosing Solutions:

PEG7-hGH, as hereinbefore defined, was prepared as follows. Methoxypoly(ethyleneglycol) was converted to the corresponding ethyl ester by titration with sodium naphthalene to generate the corresponding alkoxide, followed by reaction with ethyl bromoacetate. The ester was treated with sodium hydroxide and water to yield the corresponding carboxylic acid, α-carboxymethyl-omega-carboxymethoxy-poly(oxyethylene). This procedure is described in detail in Bückmann et al., supra.

Purification of the carboxylic acid was achieved by dissolution in warm ethanol (20 mL/g) and crystallization at 4° C. The product was isolated by filtration, washed with ether (three times) and vacuum dried. The degree of functionalization was determined by titration of a sample in aqueous solution with 0.1N KOH solution, and phenolphthaline as an indicator. Thin-layer chromatography conditions were elution with 3:17 methanol/$CH_2Cl_2$ and visualization with iodine vapor. The compound shows a streak, Rf 0 to 0.3.

The acid (15 g, 3 mmol.) was dissolved in ethyl acetate (150 mL) by warming, N-hydroxysuccinimide (0.86 g, 7.5 mmol.) and dicyclohexylcarbodiimide (1.55 g, 7.5 mmol.) were added, and the solution was stirred at 30° C. overnight (18 hours). Occasionally the product will precipitate during the reaction, in which case the thick white suspension is warmed until only the flocculent dicyclohexylurea remains out of solution. The reaction mixture was filtered through CELITE® filtration material to remove the urea, and the solution stood at 4° C. until the following morning, when the product was collected by filtration, washed with cold ethyl acetate (3 times), and dried under vacuum to give omega-methoxypoly(oxyethylene)oxyethyl-N-hydroxysuccinimide (14.7 g, 98%).

The resulting NHS-PEG was added at a 30-fold molar excess over hGH to a solution containing 12 mg/mL of hGH in 50 mM of sodium borate buffer at pH 8.5, and the solution was mixed at room temperature for one hour. The reaction mixture was then applied to a Q Sepharose (Pharmacia) column in 30 mM Tris buffer, pH 7.8, and eluted with a NaCl gradient. Then it was applied to a phenyl Toyopearl 650S column equilibrated in 0.3M sodium citrate buffer, pH 7.8. The PEGylated hGH was eluted from the column with a reverse salt gradient from 0.3 molar sodium citrate, pH 7.8, to 0 molar sodium citrate and the fractions containing PEGylated hGH of the appropriate size were pooled. The pool was then buffer-exchanged using a G25 desalting column into a buffer containing 0.25M mannitol, 0.02M glycine, and 5 mM sodium phosphate, pH 7.4, so as to have a concentration of 1.75 mg/mL. The PEG7-hGH was diluted further in the mannitol buffer so as to have a final concentration of 1 mg/mL when used in the rats for this study.

The recombinant human GH was NUTROPIN® brand hGH, 5-mg vial. Recombinant human IGF-I [available commercially from KabiGen AB, Stockholm, Sweden (specific activity>14,000 U/mg by radioreceptor assay using placental membranes) or available for clinical investigations from Genentech, Inc., South San Francisco] was employed in all the IGF-I experiments detailed in the examples. For this example, the IGF-I was dissolved at 18 mg/ml in 10 mM citrate buffer and 126 mM NaCl, pH 6.0, while for hGH the excipient was 5 mM phosphate buffer.

Animals:

Ninety-five 12- to 16-week-old female dw/dw rats (Simonsen Labs, Gilroy, Calif.) were placed on a high-fat diet consisting of one part CRISCO™ vegetable shortening to 2 parts PURINA™ powdered rodent chow. Ten age-matched rats were left on the low-fat rodent chow diet to serve as lean controls. All rats remained on their respective diet throughout the study. The animals were weighed weekly. After 8 weeks, 54 animals were chosen that had gained the most weight.

| \multicolumn{4}{c}{Experimental Design:*} | | | |
|---|---|---|---|
| Group | Daily Injection | hGH pump | IGF-I pump |
| 1 | excipient | excipient | excipient |
| 2 | excipient | hGH 300 μg | excipient |
| 3 | excipient | hGH 100 μg | excipient |
| 4 | hGH 300 μg | excipient | excipient |
| 5 | hGH 100 μg | excipient | excipient |
| 6 | excipient | excipient | IGF-I 216 μg |
| 7 | excipient | hGH 300 μg | IGF-I 216 μg |
| 8 | hGH 300 μg | excipient | IGF-I 216 μg |
| 9 | PEG7-hGH 100 μg | — | — |
| lean 10 | — | — | — |

*The doses given are μg/day.

On day −1 the rats were randomized into 9 groups of six. On day 0 obese rats were anesthetized using Ketamine/Xylazine i.p. (125:25 mg/kg). The dorsal scapular region was clipped and prepared for surgery using a 70% isopropyl alcohol swab. A small subcutaneous incision was made dorsally and two ALZA 2002 osmotic mini-pumps containing either hGH, IGF-I, or excipient were placed subcutaneously. The wound was closed using 9-mm autoclips.

Animals were injected subcutaneously with either hGH or excipient, recovered on a heated pad until ambulatory, and then placed in their home cage. Rats were injected and weighed daily and sacrificed on day 14. Lean control rats were anesthetized and sham surgeries were performed, but no mini-pumps were placed and no injections were given.

On day 14 all rats were sacrificed using $CO_2$, and serum, spleen, kidney, liver, heart, ovarian and retroperitoneal fat pads, and tibia were collected. Serum, liver, ovarian fat pads, skin, and carcass were saved and frozen. Heart and tibia were placed in formalin for histology. Serum chemistries were measured using a Monarch clinical chemistry analyzer. Serum insulin was measured by radioimmunoassay. Serum total IGF-I also was measured by radioimmunoassay, after the samples were extracted using acid/ethanol.

Results

Body Weight:

The rats fed the high-fat diet gained weight rapidly during the first four weeks of being fed the high-fat diet, but then the weight gain tended to plateau. After 8 weeks on a high-fat diet the dw/dw rats gained a large amount of weight so that 54 animals could be chosen that gained 42–83% of their initial weight, an average of 59%, compared to the range in the grain-fed rats of 18–32%, with an average gain of 23% of their initial weight.

Figure 11:
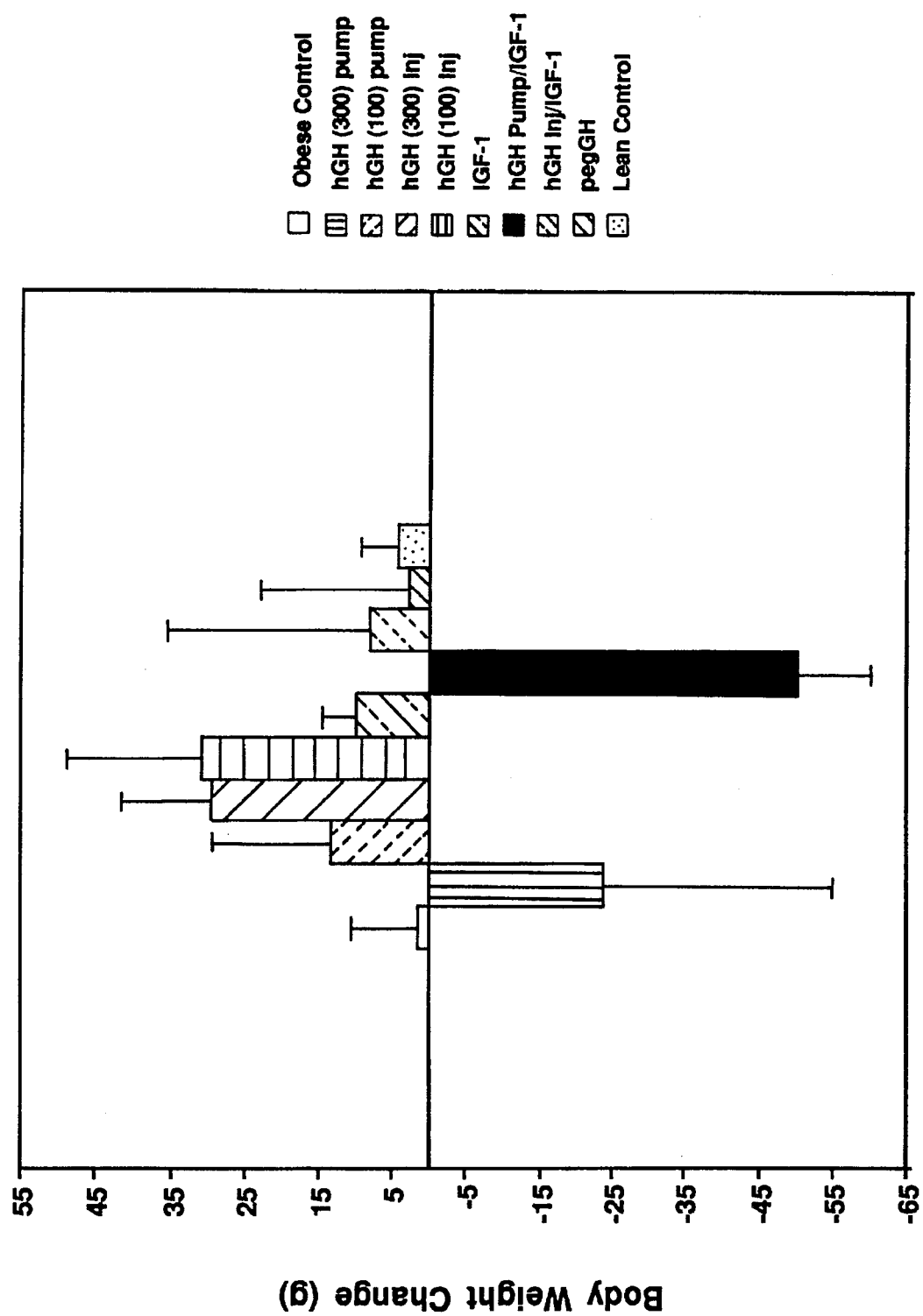
FIG. 11 shows the mean cumulative weight gains of ten groups of female dw/dw rats over 14 days of treatment. The groups were, in order from left to right: obese control (open bars), hGH 300 μg pump (solid diagonal lines), hGH 100 μg pump (intermediate shading), hGH 300 μg injection (narrow diagonal lines), hGH 100 μg injection (horizontal lines), IGF-I (dark shading), hGH pump/IGF-I (solid bar), hGH injection/IGF-I (light shading), PEG-GH (wide diagonal lines), and lean control (very light shading).

FIG. 11 shows the mean weight gains of the 10 groups of rats at pay 14. The excipient-treated rats maintained their obese state with a lack of weight gain or loss (1.5±9.0 g). After 14 days of treatment the hGH infusion and IGF-I combination showed a very consistent and very severe catabolic effect, with the average weight loss over 14 days being −50.2±10.0 g, which was significantly greater than ($p<0.05$), and over twice, that in the group receiving the 300-μg hGH infusion alone (−23.8±31.1 g). IGF-I had no significant effect on weight gain, although at 14 days weight gain occurred (10.0±4.5 g) rather than weight loss. Once again infusions of the low hGH dose of 100 μg/day gave weight gain that was not significantly different from control, but small (13.2±16.1 g) compared to the large weight gain due to 10 μg/day of hGH given by injection (30.1±18.1 g). The two doses of hGH given by injections were not different from each other but did have an anabolic effect that was statistically different ($p<0.05$) from that of the control animals. At day 14 the weight gain of the rats given daily injections of 100 μg/day PEG7-hGH (2.6±20 g) was significantly less ($p<0.05$) than that of rats given daily injections of hGH.

Figure 12:
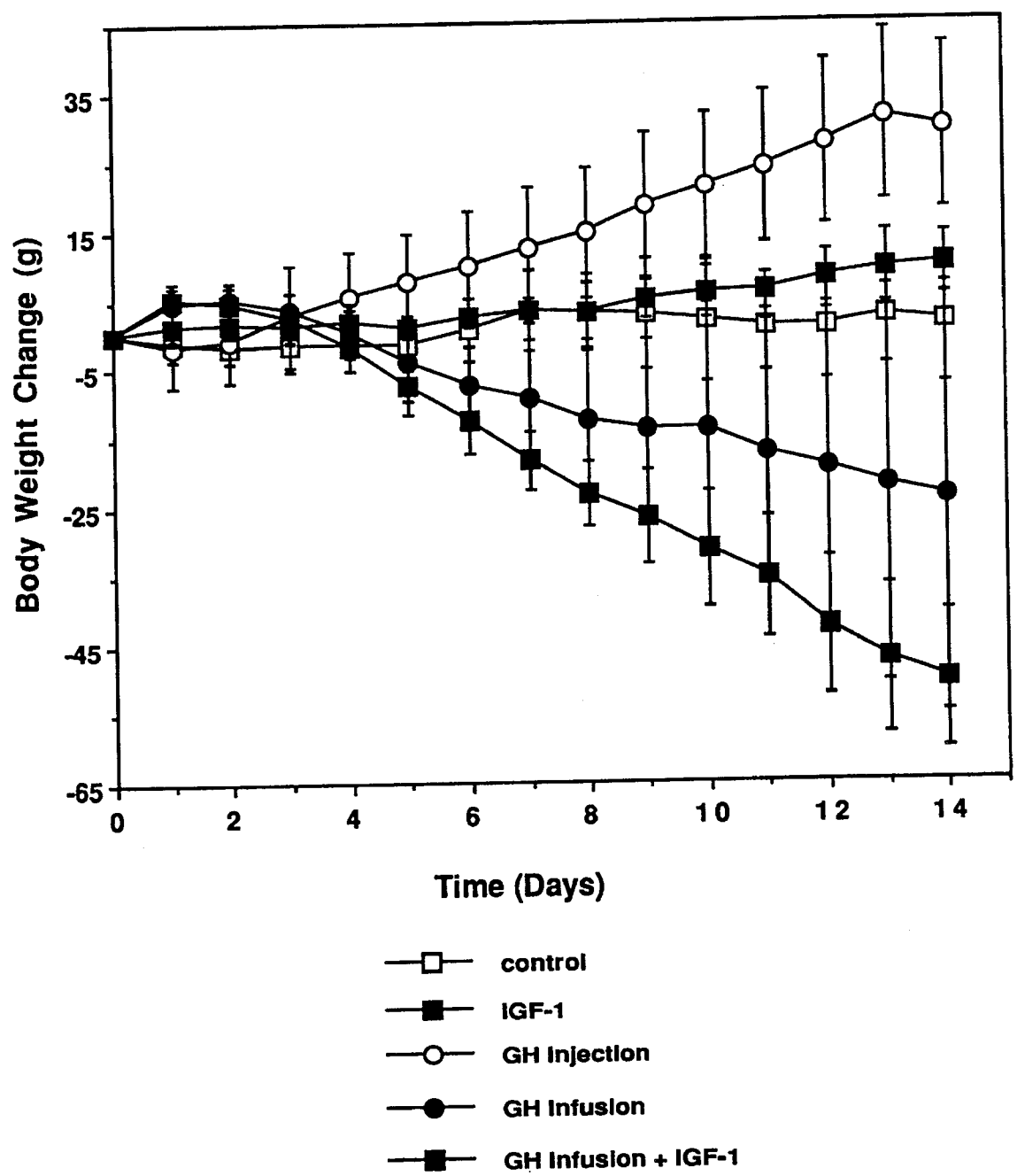
FIG. 12 shows the cumulative daily body weight changes over 14 days treatment in obese female dw/dw rats. The groups were: control (open squares), IGF-I (solid squares), GH by daily injection (open circles), GH infusion (solid circles), and GH infusion plus IGF-I (solid squares).

FIG. 12 shows the weight gains with time for some of the groups. This figure shows the dramatic differences between the two hGH regimes and between the effect of GH alone and GH given with IGF-I.

Organ Weights:

A. Heart Weight: There was no significant difference among the groups in either absolute heart weight or heart weight expressed as a percentage of body weight (relative weight).

B. Kidney weight: High-dose hGH infusions tended to increase absolute kidney weight, and dramatically increased relative kidney weight compared to controls or animals treated with GH by injection. IGF-I-treated rats had significantly larger kidneys than those of the obese controls but were no different statistically from those of the lean controls. There was a dose-related effect on relative kidney size in the hGH infusion groups. PEG7-hGH had no significant effect on kidney size.

C. Liver weight: Rats receiving the 300-μg infusions of hGH had significantly larger livers relative to body weight than those of the controls. IGF-I had no statistical effect when compared to control and had no additive effect when given in combination with hGH when compared to the high-dose hGH infusion group. hGH injection had no significant effect on relative liver size.

D. Spleen weight: Spleen weights of rats receiving IGF-I alone were significantly larger than those receiving IGF-I in combination with hGH infusions. This suggests that the spleen growth response to IGF-I was blocked by hGH infusion. These data were not expected, as effects of IGF-I so dramatically blocked by hGH infusion had not previously been seen.

Figure 13:
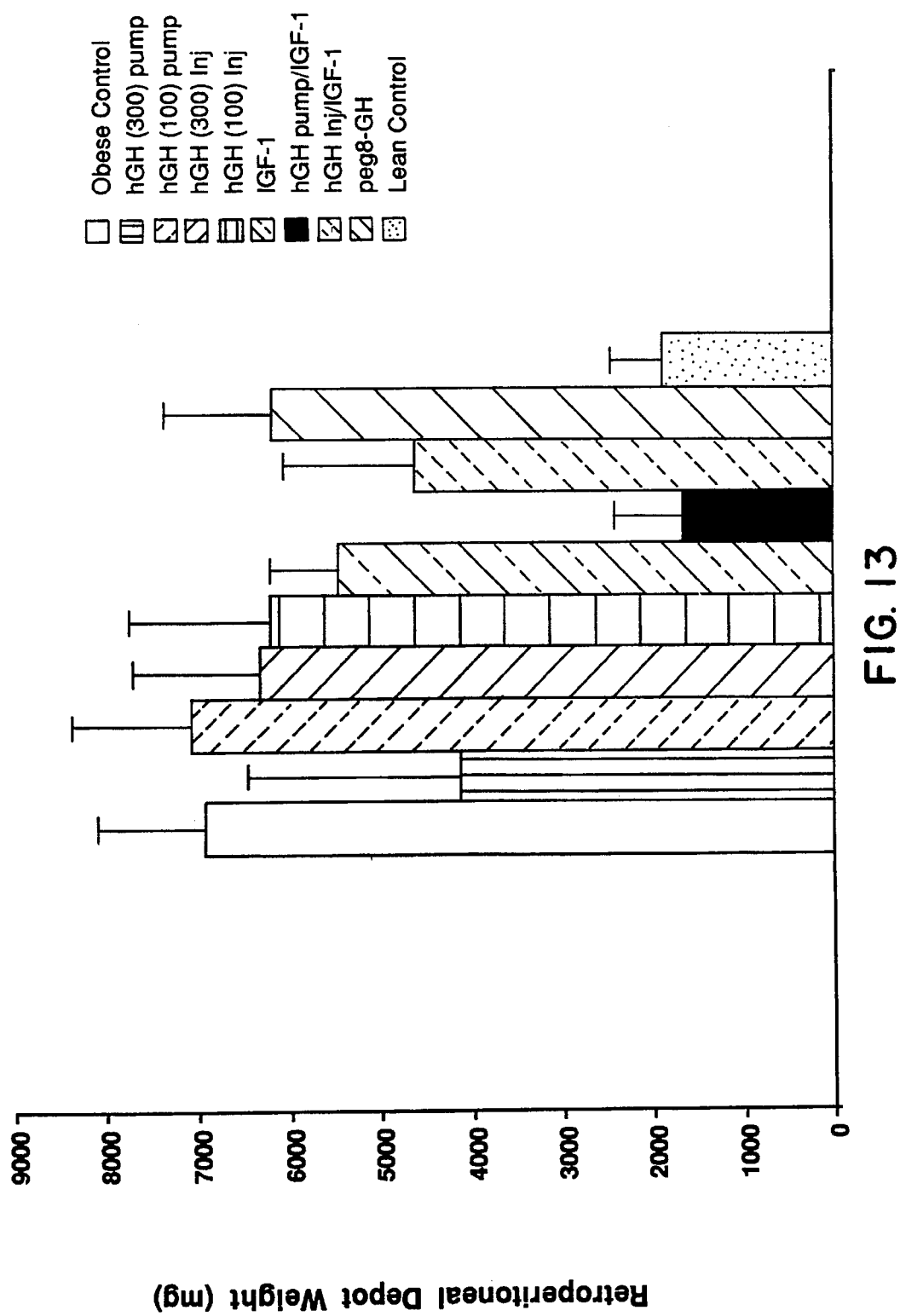
FIG. 13 shows the retro-peritoneal fat pad weight after 14 days treatment for the ten groups of female dw/dw rats, where the key is described in the legend for FIG. 11 above.
Figure 14:
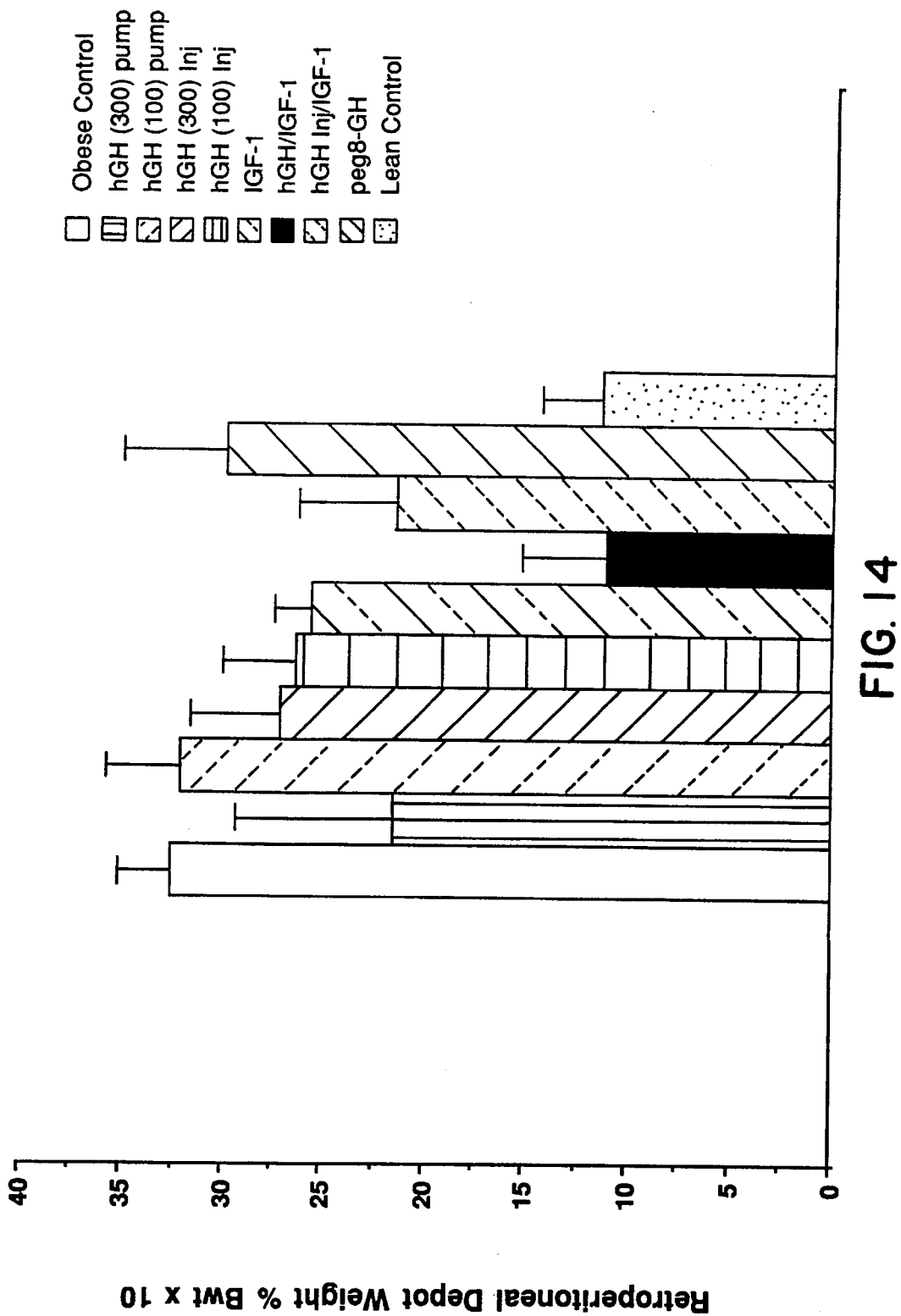
FIG. 14 shows the retro-peritoneal fat pad/body weight ratio (×10) after 14 days treatment for the ten groups of female dw/dw rats, where the key is described in the legend for FIG. 11 above.
Figure 15:
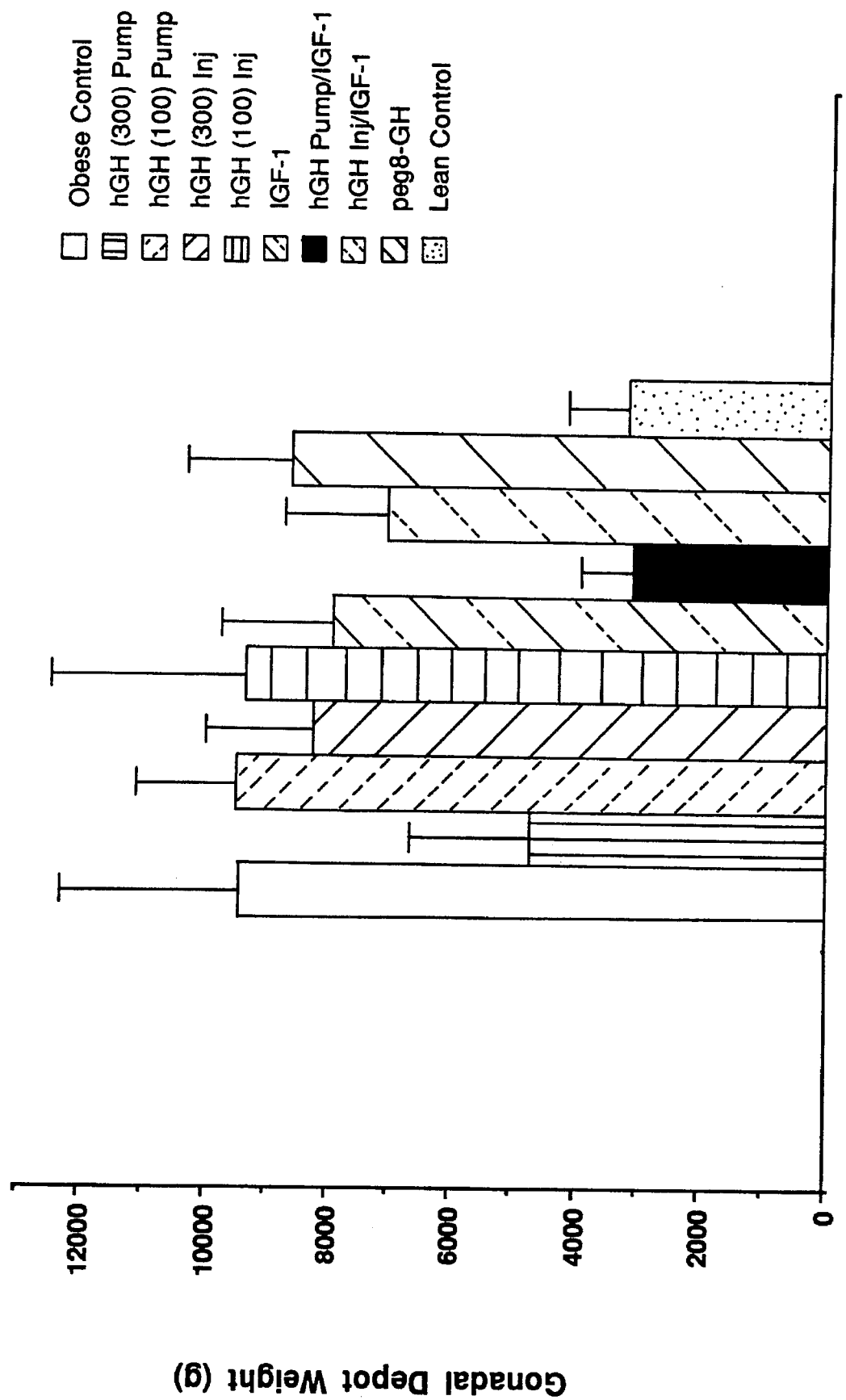
FIG. 15 shows the gonadal fat pad weight after 14 days for the ten groups of female dw/dw rats, where the key is described in the legend for FIG. 11 above.

E. Fat pads weight: The absolute retroperitoneal fat pad weight (FIG. 13) and relative weight (FIG. 14) and absolute gonadal fat pad weight (FIG. 15) are shown. The rats receiving 300 μg of hGH by infusion lost weight dramatically and had significantly ($p<0.01$) smaller adipose fat depots than controls. The 100-μg hGH infusion had a lesser effect on fat mass and the fat pads weighed significantly more ($p<0.01$) than the high-dose infusion fat pads. In contrast, the rats receiving hGH injections at either 100 or 300 μg/day had no change in the absolute weight of the retroperitoneal or gonadal depots. IGF-I alone and PEG7-hGH had no significant effect on fat-pad mass.

IGF-I infusion when given in combination with hGH injections lost significantly ($p<0.05$) more fat-pad mass than that of control, and the largest effect on body composition was that of combined GH infusions and IGF-I infusions. In this latter group the adipose mass was dramatically reduced to that of control grain-fed rats, and was reduced ($p<0.05$) compared to the group receiving GH infusion alone.

Figure 16:
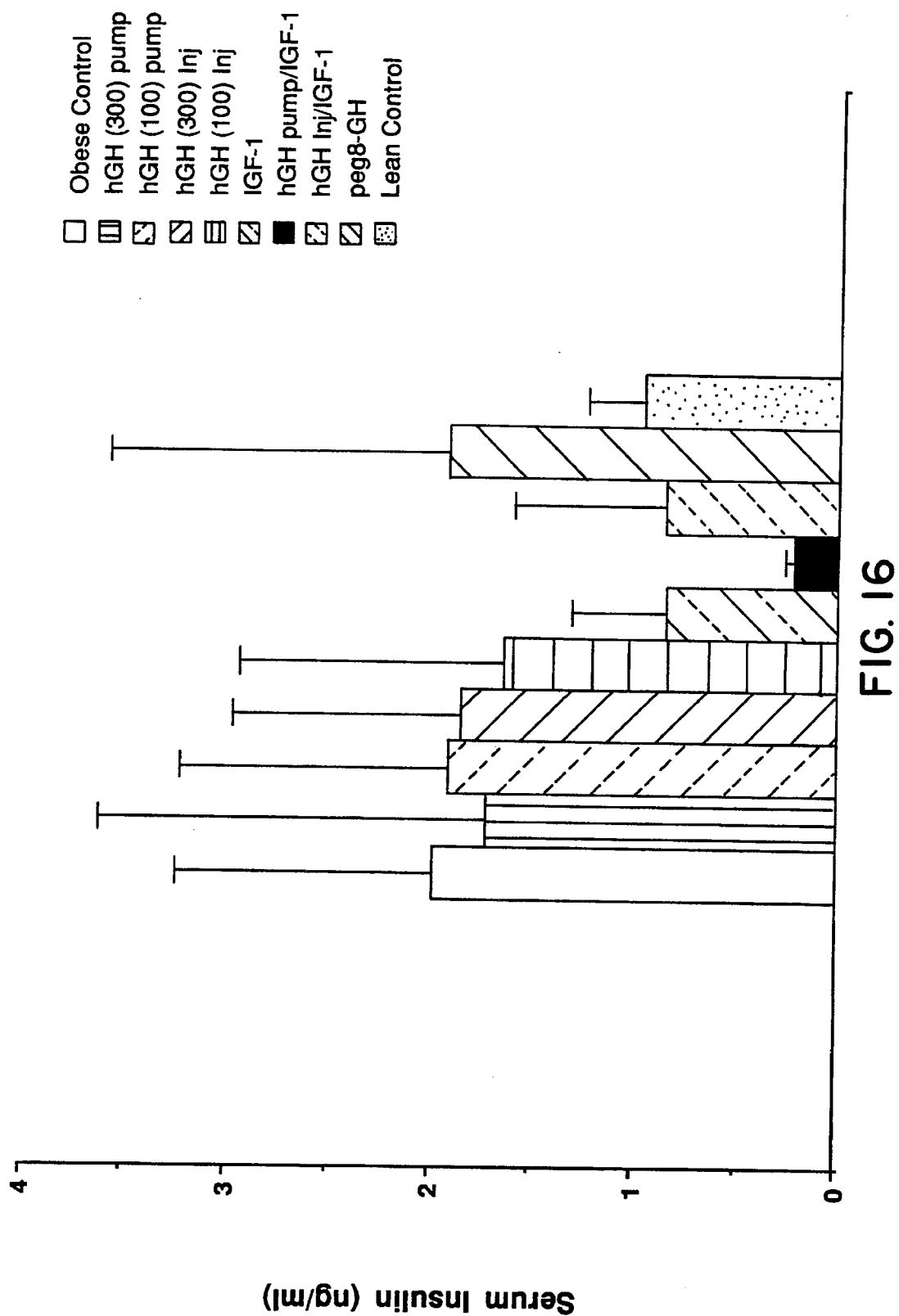
FIG. 16 shows the serum insulin levels after 14 days in the ten groups of female dw/dw rats, where the key is described in the legend for FIG. 11 above.

F. Serum Chemistries:

1. Rat insulin: By ANOVA insulin levels were not statistically different overall. See FIG. 16. But it should be noted that in the hGH infusion/IGF-I combination treatment group most animals had insulin concentrations that were ≦0.2 ng/ml, which is the minimum detectable level for this assay. It therefore appeared that IGF-I reduced insulin levels and that GH infusions plus IGF-I infusions reduced the insulin levels even further.

Figure 17:
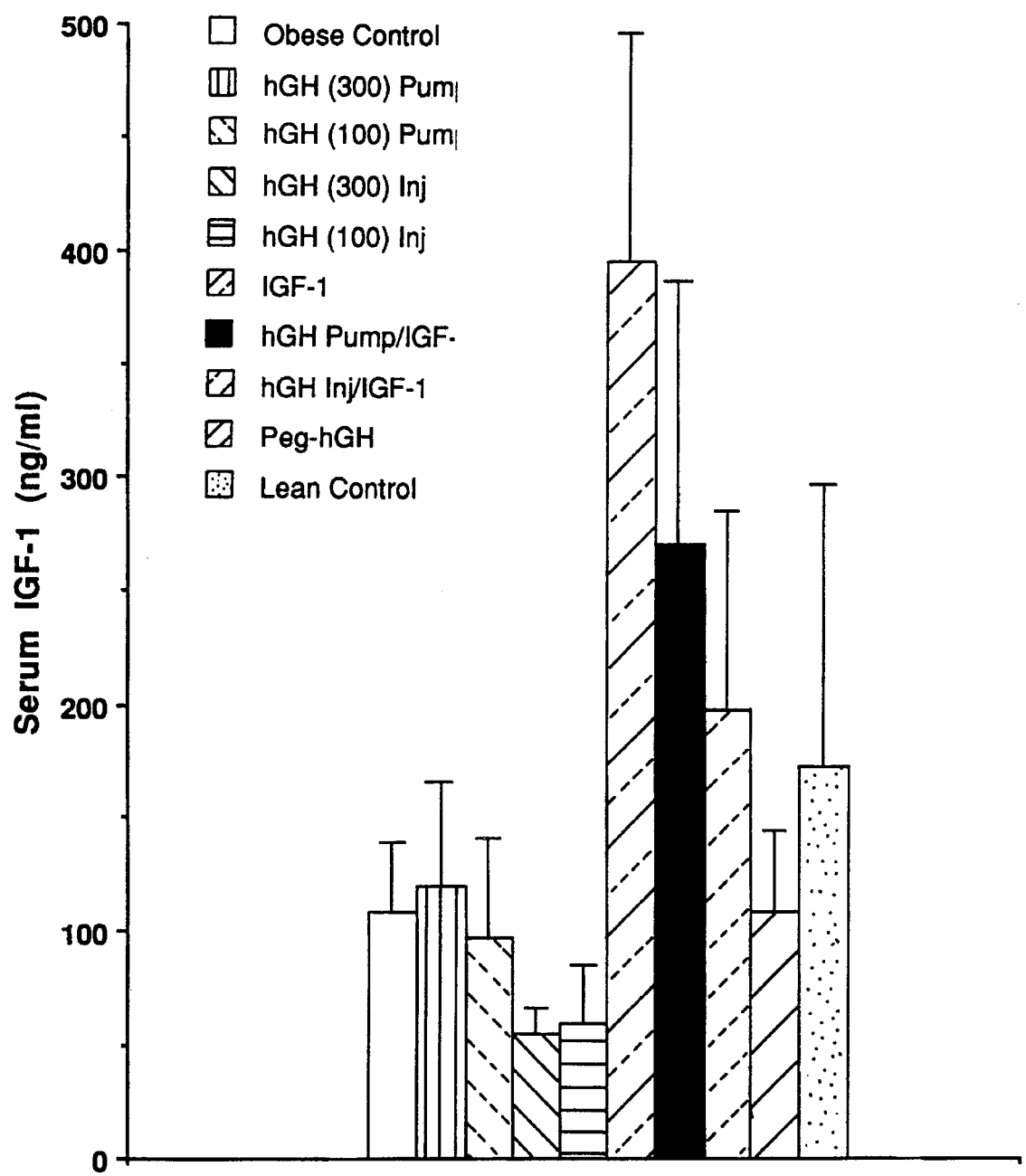
FIG. 17 shows the serum IGF-I levels after 14 days in the ten groups of female dw/dw rats, where the key is described in the legend for FIG. 11 above.

2. Serum IGF-I: Serum IGF-I concentrations in the obese rats were not affected by GH infusions (confirming the data in Table IV). See FIG. 17. As might be expected, IGF-I infusions increased serum IGF-I concentrations. But these concentrations were decreased by GH co-administration.

Figure 18:
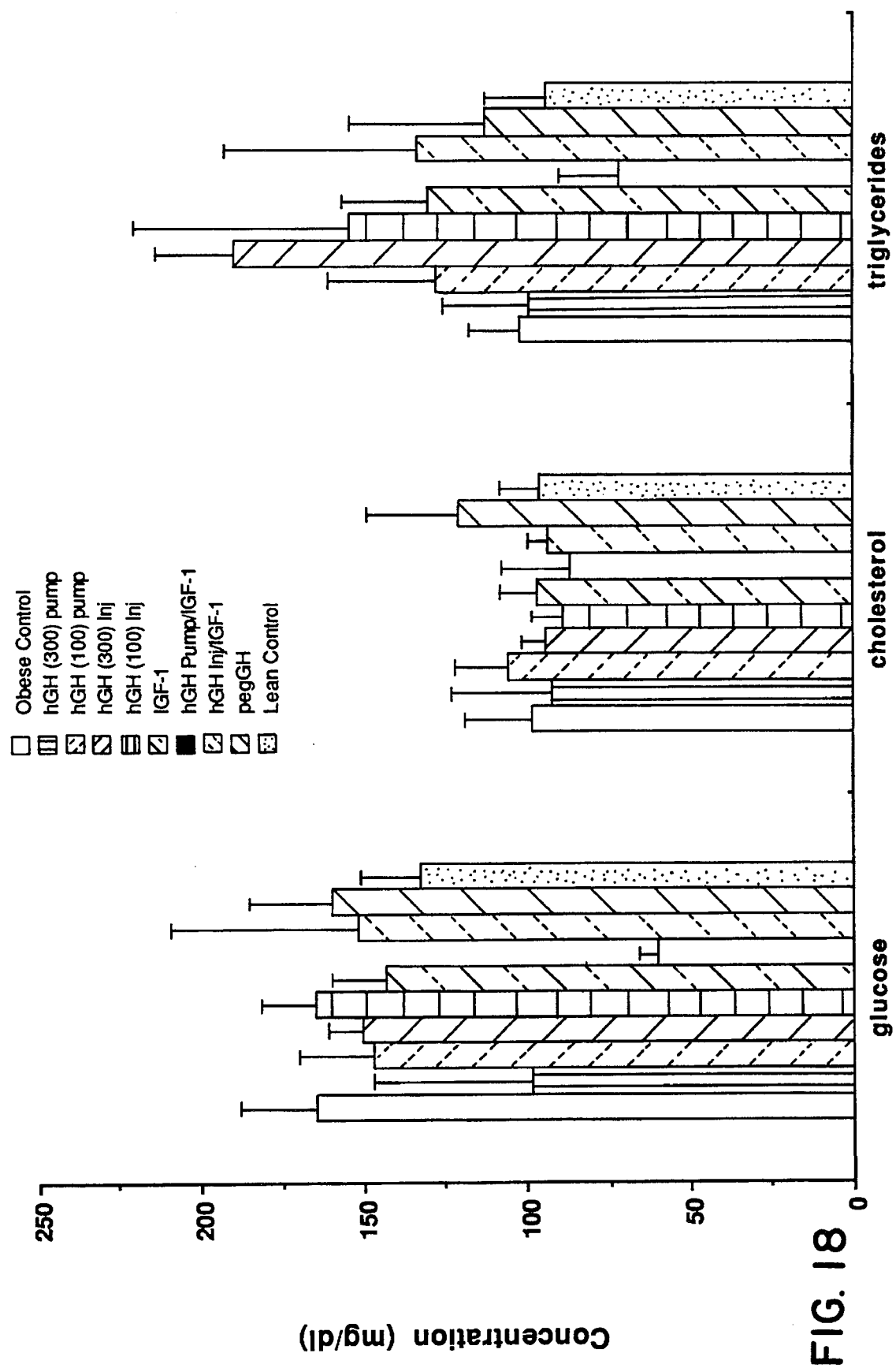
FIG. 18 shows the serum levels (mg/dl) of glucose, cholesterol, and triglycerides after 14 days in the ten groups of female dw/dw rats, where the key is described in the legend for FIG. 11 above.

3. Glucose: Glucose levels were dramatically lower in the hGH/IGF-I infusion group (59.6 mg/dl±6.3) as were the glucose levels of the high-dose hGH infusion group (98.2 mg/dl±48.9). See FIG. 18. Based on the data from Example II, food intake in the hGH infusion group is back to normal by day 14, yet glucose levels are low. PEG7-hGH had no effect on serum glucose.

4. Triglycerides: The serum triglycerides were significantly reduced when hGH and IGF-I were infused in combination. Infusions of IGF-I or hGH alone had no significant effect on serum triglycerides. Daily injections of hGH significantly increased serum triglycerides; however, when IGF-I was infused in combination with hGH injections, serum triglycerides were not statistically different from that of control. See FIG. 18. PEG7-hGH had no effect on serum triglycerides.

5. Cholesterol: There was no significant difference among groups. See FIG. 18.

Figure 19:
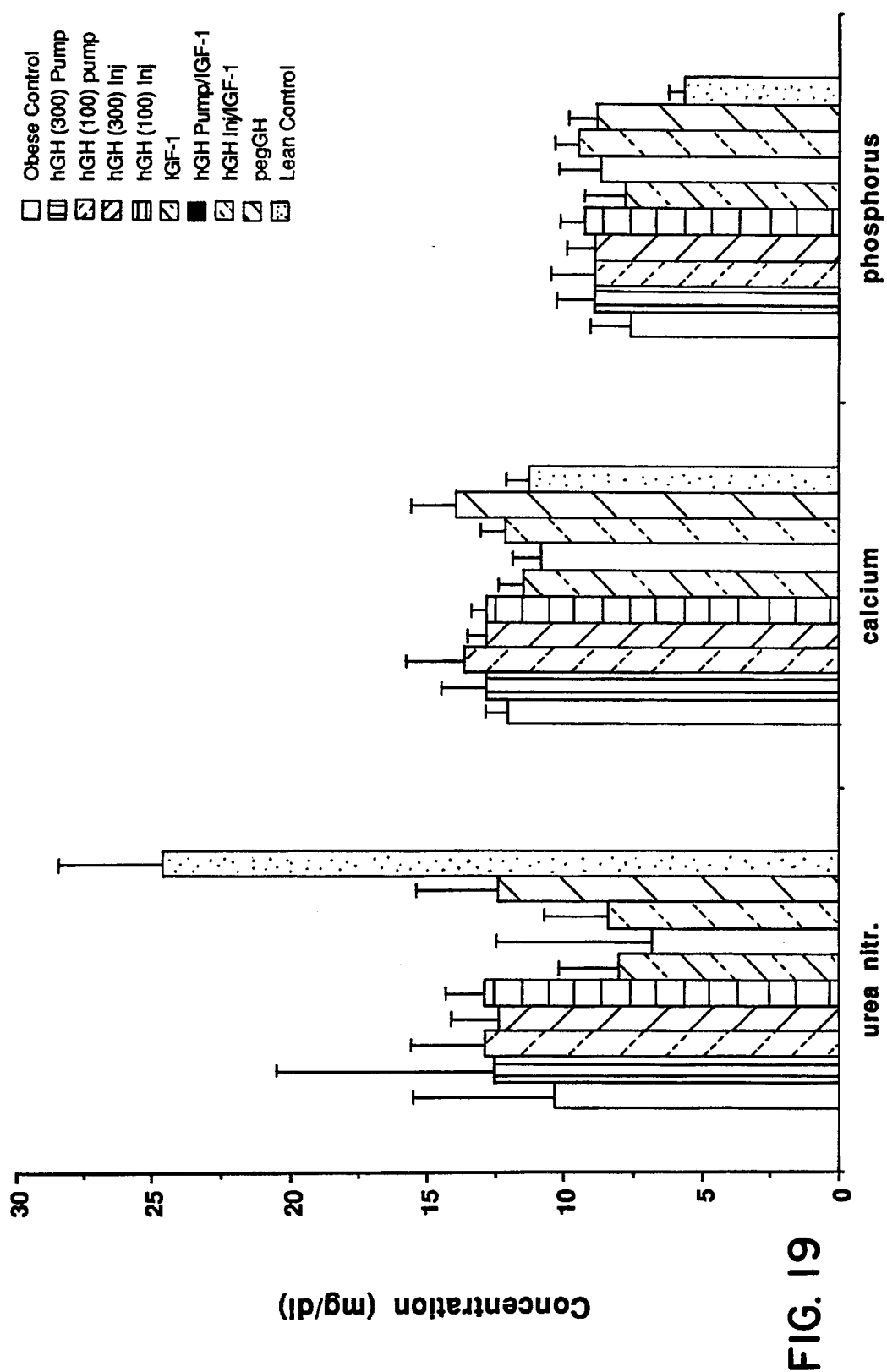
FIG. 19 shows the serum levels (mg/dl) of urea nitrogen, calcium, and phosphorus after 14 days in the ten groups of female dw/dw rats, where the key is described in the legend for FIG. 11 above.

6. Urea nitrogen: The obese rats have lower blood urea nitrogen (BUN) levels. See FIG. 19. These rats were maintained on a high-fat diet so the thin rats were eating more protein relative to calories. The groups receiving IGF-I have lower mean BUNs than the groups receiving hGH alone.

7. Calcium: Calcium was increased by hGH infusion and by PEG7-hGH but decreased if IGF-I was given alone or in combination with hGH. See FIG. 19.

8. Phosphorus: Phosphorus was high in all the obese rats. The lean controls were significantly lower. See FIG. 19.

Conclusions

The results from these studies confirm the studies in Examples I and II that the continuous administration of hGH to dietary obese animals is lipolytic and causes a dramatic loss in body weight. In contrast, the same dose of GH given by daily injection increases body weight and has no net lipolytic activity. This study now shows that the effect is dose-related.

In addition, IGF-I was employed in combination with hGH to determine if IGF-I would antagonize the lipolytic effect of the hGH infusions. Surprisingly it was found that the combination was even more effective as a lipolytic treatment than GH alone, especially when GH was infused.

In the non-obese animal IGF-I infusions and GH injections have an additive anabolic effect, but IGF-I combined with GH infusions does not have an additive anabolic effect. See U.S. Pat. No. 5,126,324, supra. It was therefore unexpected that the combination of IGF-I and GH (IGF-I infusions and GH infusions or GH injections) induced a lipolytic effect in obese mammals. Particularly surprising was the dramatic synergistic effect of GH infusion and IGF-I infusion on weight loss and on adipose tissue mass that occurred in obese rats.

Example I showed that the obese dw/dw rats became insulin resistant. GH is considered "diabetogenic," i.e., causing insulin resistance. Therefore, the administration of GH especially with IGF-I to an obese animal, where blood glucose falls (rather than rises) and insulin falls (rather than rises) is contrary to the predicted outcome.

From the surprising results herein, reducing body fat to near pre-obese levels would be expected to restore insulin sensitivity, so that in obese humans receiving insulin treatment, the appropriate administration of GH and IGF-I as described herein would allow insulin administration to be reduced or stopped. Therapy with GH and IGF-I therefore is expected to prevent, or prevent the progression of, human type II diabetes in the obese patient.

It would be reasonably expected that the rat data herein may be extrapolated to horses, cows, and other mammals, correcting for the body weight of the mammal in accordance with recognized veterinary and clinical procedures. Using standard protocols and procedures, the veterinarian or clinician will be able to adjust the doses, scheduling, and mode of administration of IGF-I and GH and their variants to achieve maximal effects in the desired mammal being treated. Humans are believed to respond in this manner as well, and do so respond as shown in Example IV below.

EXAMPLE IV

Use of GH, IGF-I, or GH and IGF-I to Treat Human Patients

Clinical data were obtained from male AIDS patients with an average age of 39 years comparing control, IGF-I alone, GH alone, and GH and IGF-I together. In these studies, IGF-I, produced and formulated as described in Example III, was administered to the AIDS patients subcutaneously at a dose of 5 mg twice daily (about 80 µg/kg twice daily considering an average body weight of 60 kg). GH, prepared and formulated as described in Example I, was administered to the AIDS patients subcutaneously at a dose of 1.4 mg/day (about 23 µg/kg/day considering an average body weight of 60 kg). The patients were treated for 6 or 12 weeks with this protocol.

After treatment, the change in fat mass (kg) from the baseline in each patient was measured using dual energy x-ray absorptiometry (DEXA), a well validated technique for measuring body composition in humans. There were 15 patients in each group at the start, but the number of patients remaining on the treatment after 12 weeks dropped to 9 for the control group, 6 for the GH group, 4 for the IGF-I group, and 6 for the GH and IGF-I group.

This study showed that after 12 weeks of treatment the combination of IGF-I and GH produced an average increase in lean body mass of about 7 lb. with concomitant fat loss. In the most dramatic case the patient gained 3 kg of lean body mass but lost 1 kg of fat. IGF-I alone showed no change over placebo, while GH alone showed a small increase in lean body mass without the fat loss. The results, shown by bar graph in FIG. 20 and by raw data in Table V, indicate that those receiving the combination treatment had by far the greatest loss of fat mass, suggesting a synergistic effect on fat loss when the hGH and IGF-I are administered together for 12 weeks. A similar effect was observed after six weeks of drug therapy.

TABLE V

| Fat Mass after 12 Weeks Hormone Treatment | | | |
|---|---|---|---|
| Placebo ± SD* | GH ± SD | IGF-I ± SD | GH + IGF-I ± SD |
| 0.00 ± 0.81 | 0.00 ± 0.83 | −0.20 ± .80 | −1.80 ± 1.94 |

*SD indicates standard deviation.

What is claimed is:

1. A method for reducing total body fat mass in an obese mammal comprising administering to the mammal an effective amount of IGF-I and growth hormone.

2. The method of claim 1 wherein the mammal is a human.

3. The method of claim 2 wherein the human has Type II diabetes and the need of the human for insulin is decreased upon the administration of growth hormone and IGF-I.

4. The method of claim 2 wherein the growth hormone is human native-sequence, mature growth hormone.

5. The method of claim 2 wherein the IGF-I is human native-sequence, mature IGF-I.

6. The method of claim 4 wherein the IGF-I is human native-sequence, mature IGF-I.

7. The method of claim 1 wherein the administration of IGF-I is be continuous infusion.

8. The method of claim 1 wherein the IGF-I is in a sustained- release formulation.

9. The method of claim 1 wherein the administration of growth hormone is by injection.

10. The method of claim 1 wherein the growth hormone is administered such that its therapeutically effective concentration is maintained continuously in the blood of the mammal for the duration of the period of its administration.

11. The method of claim 10 wherein the administration of growth hormone is by continuous infusion.

12. The method of claim 10 wherein the growth hormone is in a sustained-release formulation.

13. The method of claim 10 wherein the growth hormone is covalently conjugated via up to ten amino acid residues to a water-soluble polymer selected from the group consisting of polyethylene glycol homopolymers and polyoxyethylene polyols.

14. The method of claim 10 wherein the growth hormone is covalently conjugated to polyethylene glycol via 2 to 8 lysine residues on the growth hormone.

15. The method of claim 1 wherein the growth hormone is administered with a growth hormone binding protein.

16. The method of claim 1 wherein the effective amount of growth hormone is at least 0.01 mg/kg/day.

17. the method of claim 1 wherein the effective amount of IGF-I is at least 0.01 mg/kg/day.

18. The method of claim 1 wherein the growth hormone and IGF-I are administered separately.

19. The method of claim 1 wherein the growth hormone and IGF-I are administered as a single formulation.

20. The method of claim 1 wherein the IGF-I is administered with an IGF binding protein.

* * * * *

UNITED STATES PATENT AND TRADEMARK OFFICE
CERTIFICATE OF CORRECTION

PATENT NO. : 5,597,797
DATED : January 28, 1997
INVENTOR(S) : Ross G. Clark

It is certified that error appears in the above-indentified patent and that said Letters Patent is hereby corrected as shown below:

In column 33, claim 7, line 26, replace "be" with -- by --.

Signed and Sealed this

First Day of April, 1997

Attest:

BRUCE LEHMAN

Attesting Officer

Commissioner of Patents and Trademarks